(12) United States Patent
Bruchman et al.

(10) Patent No.: US 9,554,900 B2
(45) Date of Patent: Jan. 31, 2017

(54) DURABLE HIGH STRENGTH POLYMER COMPOSITES SUITABLE FOR IMPLANT AND ARTICLES PRODUCED THEREFROM

(71) Applicant: W. L. Gore & Associates, Inc., Newark, DE (US)

(72) Inventors: William C. Bruchman, Camp Verde, AZ (US); Paul D. Gassler, Lincoln University, PA (US); Cody L. Hartman, Flagstaff, AZ (US); Peter J. Walsh, Elkton, MD (US); Charles F. White, Camp Verde, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 787 days.

(21) Appl. No.: 13/798,595

(22) Filed: Mar. 13, 2013

(65) Prior Publication Data

US 2013/0325117 A1 Dec. 5, 2013

Related U.S. Application Data

(63) Continuation-in-part of application No. 13/078,774, filed on Apr. 1, 2011, now Pat. No. 8,961,599.

(51) Int. Cl.
*A61F 2/24* (2006.01)
*A61L 27/48* (2006.01)
*A61L 27/50* (2006.01)

(52) U.S. Cl.
CPC .......... *A61F 2/2415* (2013.01); *A61F 2/2412* (2013.01); *A61F 2/2418* (2013.01); *A61L 27/48* (2013.01); *A61L 27/507* (2013.01); *A61F 2/2472* (2013.01); *A61F 2220/0075* (2013.01); *A61F 2230/0054* (2013.01); *Y10T 156/10* (2015.01)

(58) Field of Classification Search
CPC ......... A61F 2/24; A61F 2/2415; A61F 2/2418
USPC .................................. 623/2.1–2.19
See application file for complete search history.

(56) References Cited

U.S. PATENT DOCUMENTS

| | | |
|---|---|---|
| 3,953,566 A | 4/1976 | Gore |
| 4,339,831 A | 7/1982 | Johnson |
| 4,340,091 A | 7/1982 | Skelton et al. |

(Continued)

FOREIGN PATENT DOCUMENTS

| | | |
|---|---|---|
| EP | 150608 | 8/1985 |
| EP | 293090 | 11/1988 |

(Continued)

OTHER PUBLICATIONS

International Search Report and Written Opinion for PCT/US2012/031417 mailed Oct. 18, 2012, corresponding to U.S. Appl. No. 13/078,774.

(Continued)

*Primary Examiner* — Suzette J Gherbi
(74) *Attorney, Agent, or Firm* — Paul J. Fordenbacher, Esq

(57) ABSTRACT

Thin, biocompatible, high-strength, composite materials are disclosed that are suitable for use in a valve for regulating blood flow direction. In one aspect, the composite material maintains flexibility in high-cycle flexural applications, making it particularly applicable to high-flex implants such as a prosthetic heart valve leaflet. The composite material includes a porous polymer membrane and an elastomer, wherein the elastomer fills substantially all of the pores of the porous polymer membrane.

89 Claims, 32 Drawing Sheets

(56) References Cited

U.S. PATENT DOCUMENTS

| | | | |
|---|---|---|---|
| 4,629,459 A | 12/1986 | Ionescu et al. | |
| 4,955,899 A | 9/1990 | Della | |
| 5,071,609 A | 12/1991 | Tu et al. | |
| 5,708,044 A | 1/1998 | Branca | |
| 6,451,396 B1 | 9/2002 | Zumbrum | |
| 6,541,589 B1 | 4/2003 | Baillie | |
| 6,673,455 B2 | 1/2004 | Zumbrum | |
| 6,770,579 B1* | 8/2004 | Dawson | A41D 31/00 428/131 |
| 6,776,604 B1 | 8/2004 | Chobotov et al. | |
| 7,306,729 B2 | 12/2007 | Bacino | |
| 7,462,675 B2 | 12/2008 | Chang et al. | |
| 7,531,611 B2 | 5/2009 | Sabol et al. | |
| 7,628,803 B2 | 12/2009 | Pavcnik et al. | |
| 7,789,908 B2 | 9/2010 | Sowinski et al. | |
| 8,637,144 B2 | 1/2014 | Ford | |
| 2001/0051824 A1 | 12/2001 | Hopkins | |
| 2003/0004559 A1 | 1/2003 | Lentz et al. | |
| 2003/0012905 A1* | 1/2003 | Zumbrum | B32B 5/32 428/36.4 |
| 2003/0055492 A1 | 3/2003 | Shaolian et al. | |
| 2003/0055495 A1 | 3/2003 | Pease et al. | |
| 2003/0211264 A1 | 11/2003 | Farnsworth et al. | |
| 2004/0019374 A1 | 1/2004 | Hojeibane et al. | |
| 2004/0024448 A1 | 2/2004 | Chang et al. | |
| 2005/0137682 A1 | 6/2005 | Justino | |
| 2006/0259133 A1 | 11/2006 | Sowinski et al. | |
| 2007/0027535 A1 | 2/2007 | Purdy | |
| 2007/0118210 A1 | 5/2007 | Pinchuk | |
| 2008/0091261 A1 | 4/2008 | Long et al. | |
| 2008/0125711 A1 | 5/2008 | Alpini et al. | |
| 2008/0133004 A1 | 6/2008 | White | |
| 2009/0004239 A1* | 1/2009 | Ladet | A61F 2/02 424/423 |
| 2009/0187197 A1* | 7/2009 | Roeber | A61F 2/0063 606/151 |
| 2010/0190254 A1* | 7/2010 | Chian | A61L 27/3847 435/396 |
| 2010/0248324 A1 | 9/2010 | Xu et al. | |
| 2010/0249922 A1* | 9/2010 | Li | A61F 2/2412 623/2.17 |
| 2011/0039690 A1* | 2/2011 | Niu | B01D 39/083 502/184 |
| 2011/0142804 A1* | 6/2011 | Gaudette | A61L 27/18 424/93.7 |
| 2011/0250689 A1* | 10/2011 | Baaijens | D01D 5/0076 435/398 |
| 2011/0311746 A1* | 12/2011 | Ma | A61L 27/56 428/36.91 |
| 2012/0058100 A1* | 3/2012 | Shastri | A61K 47/34 424/94.4 |
| 2012/0061314 A1* | 3/2012 | Choi | B01D 67/0088 210/490 |
| 2012/0129150 A1* | 5/2012 | Carbonell | B01D 15/00 435/4 |
| 2012/0253453 A1* | 10/2012 | Bruchman | A61L 27/48 623/1.24 |
| 2012/0290082 A1 | 11/2012 | Quint et al. | |
| 2012/0296418 A1* | 11/2012 | Bonyuet | A61F 2/2415 623/2.18 |
| 2012/0323315 A1* | 12/2012 | Bruchman | A61F 2/2415 623/2.17 |
| 2013/0150947 A1* | 6/2013 | Kaufmann | A61L 27/18 623/1.15 |
| 2013/0310924 A1* | 11/2013 | Groothuis | A61F 2/2412 623/2.11 |
| 2014/0180400 A1 | 6/2014 | Bruchman et al. | |
| 2014/0288642 A1* | 9/2014 | Yoshida | A61L 27/16 623/2.17 |
| 2015/0224231 A1* | 8/2015 | Bruchman | A61F 2/2418 623/2.17 |
| 2015/0257876 A1* | 9/2015 | Bruchman | A61F 2/2415 623/2.17 |
| 2015/0265744 A1* | 9/2015 | Baaijens | A61F 2/24 435/396 |
| 2015/0283297 A1* | 10/2015 | Baaijens | A61F 2/24 623/2.1 |
| 2015/0305862 A1* | 10/2015 | Bruchman | A61F 2/2415 156/185 |
| 2015/0306277 A1* | 10/2015 | Pathak | A61K 35/12 424/443 |
| 2015/0366663 A1* | 12/2015 | Bruchman | A61F 2/2409 623/2.18 |
| 2016/0008133 A9* | 1/2016 | Day | A61L 27/10 623/23.56 |
| 2016/0067374 A1* | 3/2016 | Puckett | A61L 27/16 442/350 |

FOREIGN PATENT DOCUMENTS

| | | |
|---|---|---|
| EP | 773971 | 5/1997 |
| EP | 1 977 719 | 10/2008 |
| WO | 95/28899 | 11/1995 |
| WO | 98/26731 | 6/1998 |
| WO | 02/100454 | 12/2002 |
| WO | 2004/000375 | 12/2003 |
| WO | 2006/000763 | 1/2006 |
| WO | 2007/002320 | 1/2007 |
| WO | 2007/016251 | 2/2007 |
| WO | 2009/038761 | 3/2009 |
| WO | 2009/149462 | 12/2009 |
| WO | 2011/065809 | 6/2011 |

OTHER PUBLICATIONS

International Search Report mailed Nov. 14, 2012 and Written Opinion for PCT/US2012/040529 corresponding to U.S. Appl. No. 13/485,823.

International Search Report and Written Opinion for PCT/US2014/016550 mailed Jul. 2, 2014, corresponding to U.S. Appl. No. 13/798,595; 9 pages.

International Search Report and Written mailed May 30, 2014, correspondin Opinion for PCT/US2014/016807 to U.S. Appl. No. 14/181,965, 4 pages.

International Search Report and Written Opinion for PCT/US2015/042530 mailed Oct. 6, 2015, corresponding to U.S. Appl. No. 14/622,599, 3 pages.

Annex to Form PCT/ISA/206 Communication Relating to the Results of the Partial International Search PCT/US2014/016550 mailed Apr. 8, 2014, corresponding to U.S. Appl. No. 13/798,595; 3 pages.

International Search Report and Written Opinion for PCT/US2014/016581 mailed Apr. 8, 2014, corresponding to U.S. Appl. No. 13/801,701; 4 pages.

* cited by examiner

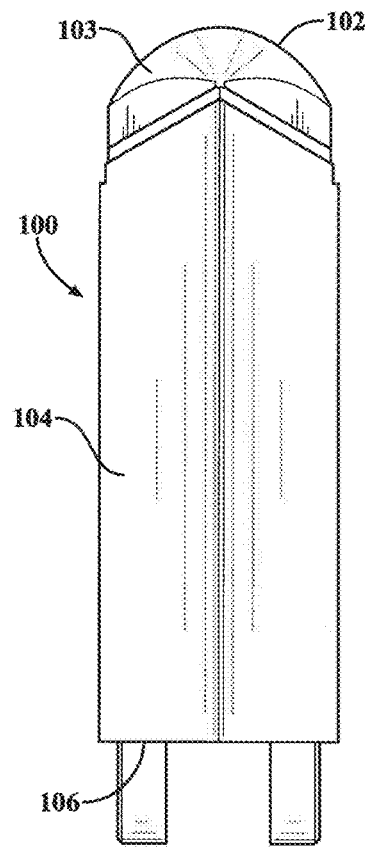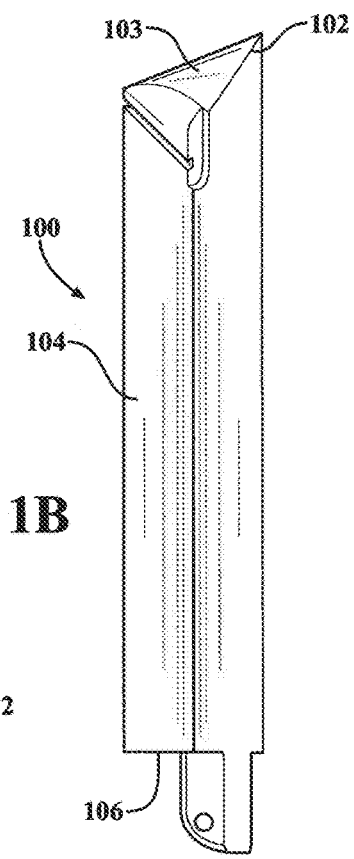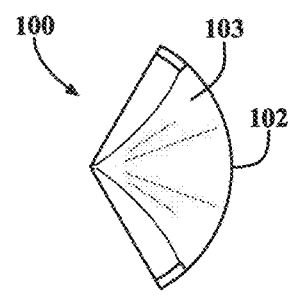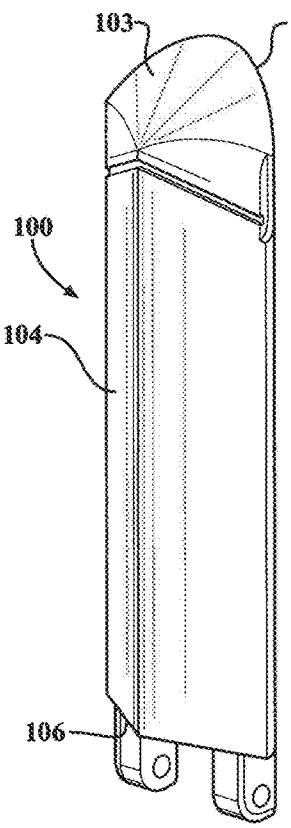
FIG. 1A
FIG. 1B
FIG. 1C
FIG. 1D

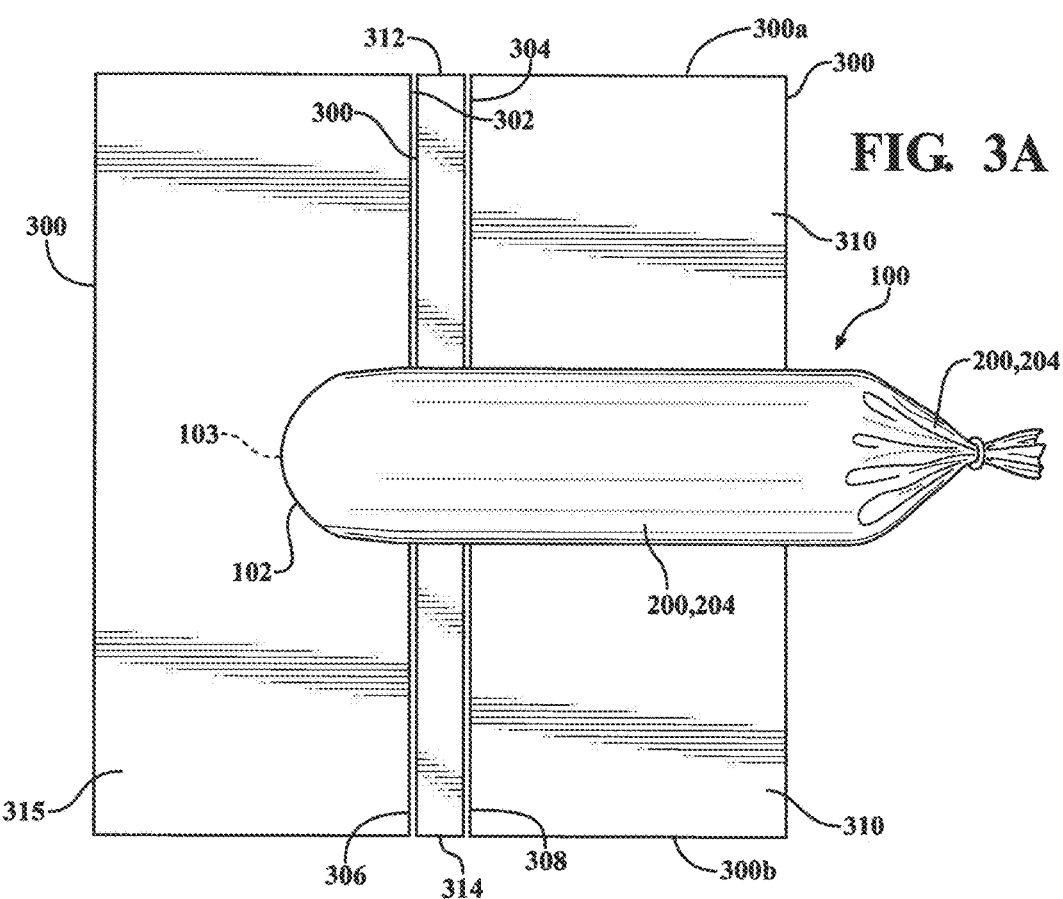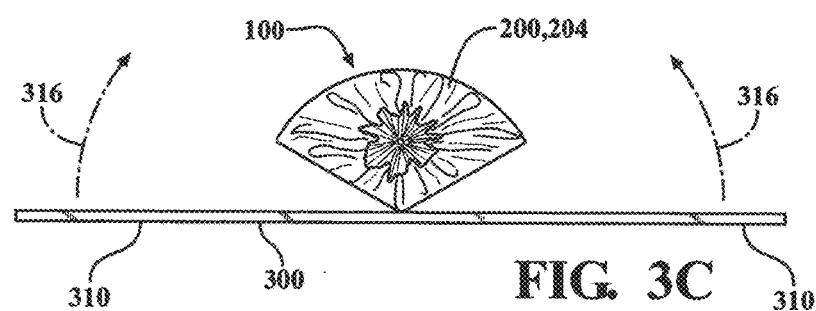

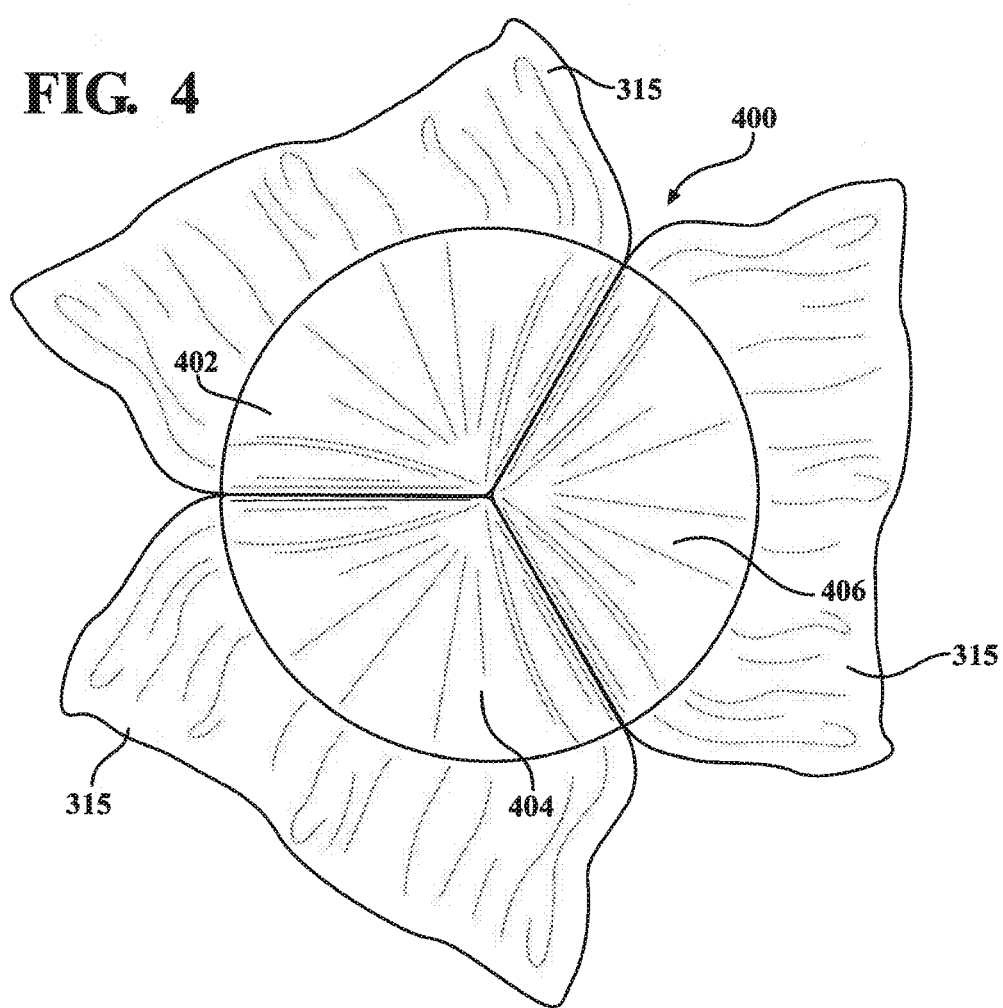

FIG. 11B

Statistics on Pressure Peaks

| Pressure Peaks | | | | | |
|---|---|---|---|---|---|
| 133.61 | 103.76 | 158.54 | 107.03 | 139.99 | 121.69 | 139.99 |

| | |
|---|---|
| Run# | 586 |
| Time Stamp | 5/11/2009@10:31 AM |
| ID | 87905 PPT PATT (stn E pp91) |
| Target Pressure (mmHg) | 95.00 |
| Datapoints/Cycle | 77.02 |
| # of Peaks | 51 |
| Max of Peaks | 158.54 |
| Min of Peaks | 101.85 |
| Mean | 126.87 |
| Standard Deviation | 14.77 |
| # Below Target | 0 |
| % Below Target | 0.00 |
| Target Distance from Mean (Std.) | -2.16 |
| Theoretical % Below Target | 1.55 |

| | |
|---|---|
| Speed (cpm) | 779 |
| Cycles | 2.47.808E+6 |

(5% when -1.645 Std. Dev. Away)

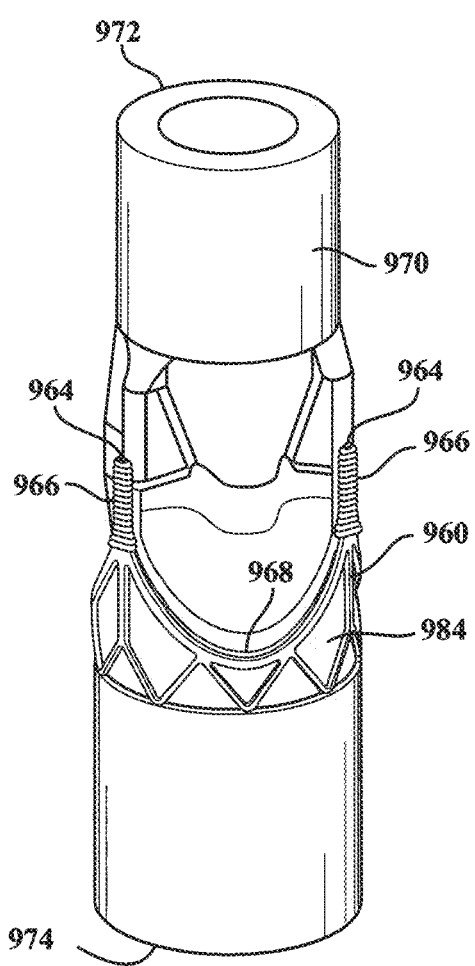
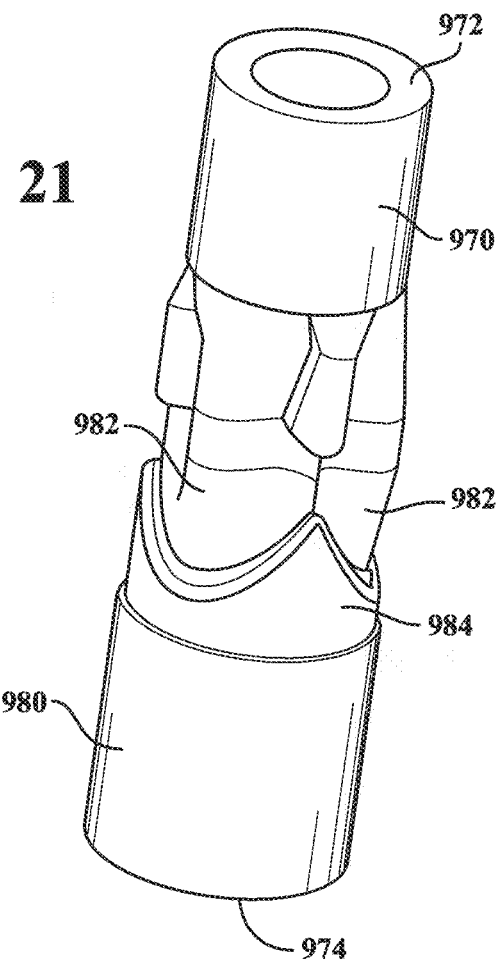
FIG. 21
FIG. 22

DURABLE HIGH STRENGTH POLYMER COMPOSITES SUITABLE FOR IMPLANT AND ARTICLES PRODUCED THEREFROM

CROSS-REFERENCE TO RELATED APPLICATIONS

This application is a continuation-in-part application of co-pending U.S. patent application Ser. No. 13/078,774 filed Apr. 1, 2011, which is herein incorporated by reference in its entirety.

FIELD

The invention relates to materials used in medical implants. More particularly, the invention relates to a biocompatible material suitable for use in high-cycle flexural applications including artificial heart valves.

BACKGROUND

Artificial heart valves preferably should last at least ten years in vivo. To last that long, artificial heart valves should exhibit sufficient durability for at least four hundred million cycles or more. The valves, and more specifically heart valve leaflets, must resist structural degradation including the formation of holes, tears, and the like as well as adverse biological consequences including calcification and thrombosis.

A variety of polymeric materials has previously been employed as prosthetic heart valve leaflets. Failure of these leaflets due to stiffening and hole formation occurred within two years of implant. Efforts to improve leaflet durability by thickening the leaflets resulted in unacceptable hemodynamic performance of the valves, that is, the pressure drop across the open valve was too high.

As such, it remains desirable to provide a biocompatible artificial heart valve design that lasts beyond ten years in vivo by exhibiting sufficient durability for at least about four hundred million cycles of flexure or more.

SUMMARY

According to an embodiment, a valve is provided for regulating blood flow direction. In an embodiment, the valve includes a leaflet comprising a composite material with at least one synthetic polymer membrane comprising fibers wherein a diameter of the majority of the fibers is less than about 1 µm, the space between the fibers defining pores, the elastomer being disposed in substantially all of the pores.

In another embodiment, the valve includes a support structure and at least one leaflet being supported on the support structure and movable between open and closed positions. Each leaflet includes a composite material comprising at least one synthetic polymer membrane and an elastomer. The at least one synthetic polymer membrane comprises fibers wherein a diameter of the majority of the fibers is less than about 1 µm. The space between the fibers define pores. The elastomer is disposed in substantially all of the pores.

In another embodiment, the valve includes a support structure and at least one leaflet supported on the support structure and movable between open and closed positions. Each leaflet includes a composite material comprising at least one synthetic polymer membrane and an elastomer. The at least one synthetic polymer membrane comprises pores with the elastomer present in substantially all of the pores. The composite material comprises synthetic polymer membrane by weight in the range of about 10% to 90%.

In another embodiment, the valve includes a support structure and at least one leaflet supported on the support structure and movable between open and closed positions. Each leaflet includes a composite material comprising at least one synthetic polymer membrane and an elastomer. The at least one synthetic polymer membrane comprises pores having a pore size less than about 5 µm with the elastomer present in substantially all of the pores.

In another embodiment, a method of forming a leaflet of a prosthetic heart valve is provided. The method comprises providing a composite material comprising at least one synthetic polymer membrane and an elastomer, the at least one synthetic polymer membrane comprising fibers wherein a diameter of the majority of the fibers is less than about 1 µm, the space between the fibers defining pores, the elastomer being disposed in substantially all of the pores; bringing more than one layer of the composite material into contact with additional layers of the composite material; and bonding the layers of composite material together.

In another embodiment, a method of forming a prosthetic heart valve including leaflets is provided. The method comprises: providing a generally annular support structure; providing a composite material comprising at least one synthetic polymer membrane and an elastomer, the at least one synthetic polymer membrane comprising fibers wherein a diameter of the majority of the fibers is less than about 1 µm, the space between the fibers defining pores, the elastomer being disposed in substantially all of the pores; wrapping the composite material about the support structure bringing more than one layer of the composite material into contact with additional layers of the composite material; and bonding the layers of composite material to itself and to the support structure.

In another embodiment, a method of forming a leaflet of a prosthetic heart valve is provided. The method comprises providing a composite material comprising at least one synthetic polymer membrane and an elastomer, the at least one synthetic polymer membrane comprising fibers, the space between the fibers defining pores that have a pore size of less than about 5 µm, the elastomer being disposed in substantially all of the pores; bringing more than one layer of the composite material into contact with additional layers of the composite material; and bonding the layers of composite material together.

In another embodiment, a method of forming a prosthetic heart valve including leaflets is provided. The method comprises: providing a generally annular support structure; providing a composite material comprising at least one synthetic polymer membrane and an elastomer, the at least one synthetic polymer membrane comprising fibers, the space between the fibers defining pores that have a pore size of less than about 5 µm, the elastomer being disposed in substantially all of the pores; wrapping the composite material about the support structure bringing more than one layer of the composite material into contact with additional layers of the composite material; and bonding the layers of composite material to itself and to the support structure.

In another embodiment, the valve includes a generally annular shaped support structure having a first end and a second end opposite the first end. The second end comprises a plurality of posts extending longitudinally therefrom. A sheet of composite material extends from post to post wherein leaflets are defined by the composite material that is between the posts. In an embodiment, a cushion member is coupled to the post and provides a cushion between the post and the leaflets to minimize stress and wear on the leaflets as the leaflets cycle between open and closed positions.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIGS. 1A, 1B, 1C, and 1D are front, side and top elevational views, and a perspective view, respectively, of a tool for forming a heart valve leaflet, in accordance with an embodiment;

FIGS. 3A, 3B and 3C are top, side and front elevational views, respectively, illustrating a step in the formation of a valve leaflet, in which the leaflet tool covered by the cushion pad and release layer (shown in FIGS. 2A and 2B, respectively) is positioned over a composite material for cutting and further assembly, in accordance with an embodiment;

FIG. 4 is a top elevational view of a tri-leaflet assembly prior to cutting excess leaflet material, in accordance with an embodiment;

FIGS. 11A and 11B are a graph and data chart, respectively, of measured outputs from a high rate fatigue tester used for measuring performance of the valve assemblies made in accordance with embodiments;

FIG. 21 is a perspective view of a stereo lithography-formed mandrel, in accordance with an embodiment;

FIG. 22 is a perspective view of the cushion-wrapped valve frame of FIG. 20 mounted onto the mandrel of FIG. 21, in accordance with an embodiment.

DETAILED DESCRIPTION

Figure 2A:
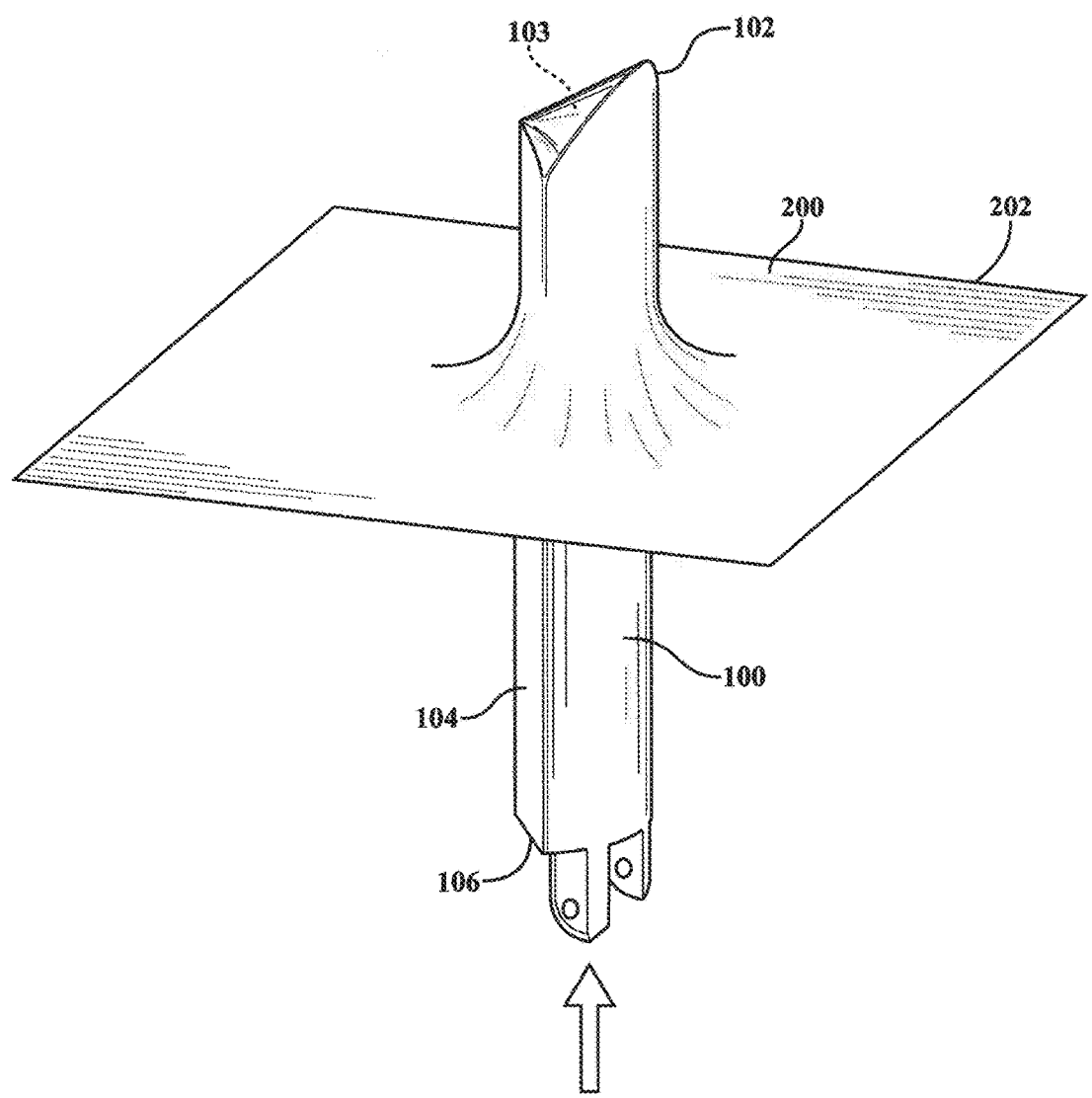
FIG. 2A is a perspective view of a cushion pad being stretched over a leaflet tool, in accordance with an embodiment.

References will now be made to embodiments illustrated in the drawings and specific language which will be used to describe the same. It will nevertheless be understood that no limitation of the scope of the invention is thereby intended, such alterations and further modifications in the illustrated methods and apparatus, as such further applications of the principles of the invention as illustrated therein as being contemplated as would normally occur to one skilled in the art to which the invention relates.

Definitions for some terms used herein are provided below in the Appendix.

The present disclosure addresses a long-felt need for a material that meets the durability and biocompatibility requirements of high-cycle flexural implant applications, such as heart valve leaflets. It has been observed that heart valve leaflets formed from porous fluoropolymer materials or, more particularly, from ePTFE containing no elastomer suffer from stiffening in high-cycle flex testing and animal implantation.

In one embodiment, described in greater detail below, the flexural durability of porous polymer heart valve leaflets was significantly increased by adding a relatively high-percentage of relatively lower strength elastomer to the pores. Optionally, additional layers of the elastomer may be added between the composite layers. Surprisingly, in embodiments wherein porous polymer membranes are imbibed with elastomer the presence of the elastomer increased overall thickness of the leaflet, the resulting increased thickness of the polymer members due to the addition of the elastomer did not hinder or diminish flexural durability. Further, after reaching a minimum percent by weight of elastomer, it was found that fluoropolymer members performed better with increasing percentages of elastomer resulting in significantly increased cycle lives exceeding 40 million cycles in vitro, as well as by showing no signs of calcification under certain controlled laboratory conditions.

A material according to one embodiment includes a composite material comprising an expanded fluoropolymer membrane and an elastomeric material. It should be readily appreciated that multiple types of fluoropolymer membranes and multiple types of elastomeric materials can be combined while within the spirit of the present invention. It should also be readily appreciated that the elastomeric material can include multiple elastomers, multiple types of non-elastomeric components, such as inorganic fillers, therapeutic agents, radiopaque markers, and the like while within the spirit of the present invention.

In some embodiments, the composite material includes an expanded fluoropolymer material made from porous ePTFE membrane, for instance as generally described in U.S. Pat. No. 7,306,729. In some other embodiments, the composite material includes a polyethylene material made from porous polyethylene membrane.

The expandable fluoropolymer, used to form the expanded fluoropolymer material described in embodiments, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

Figure 7A:
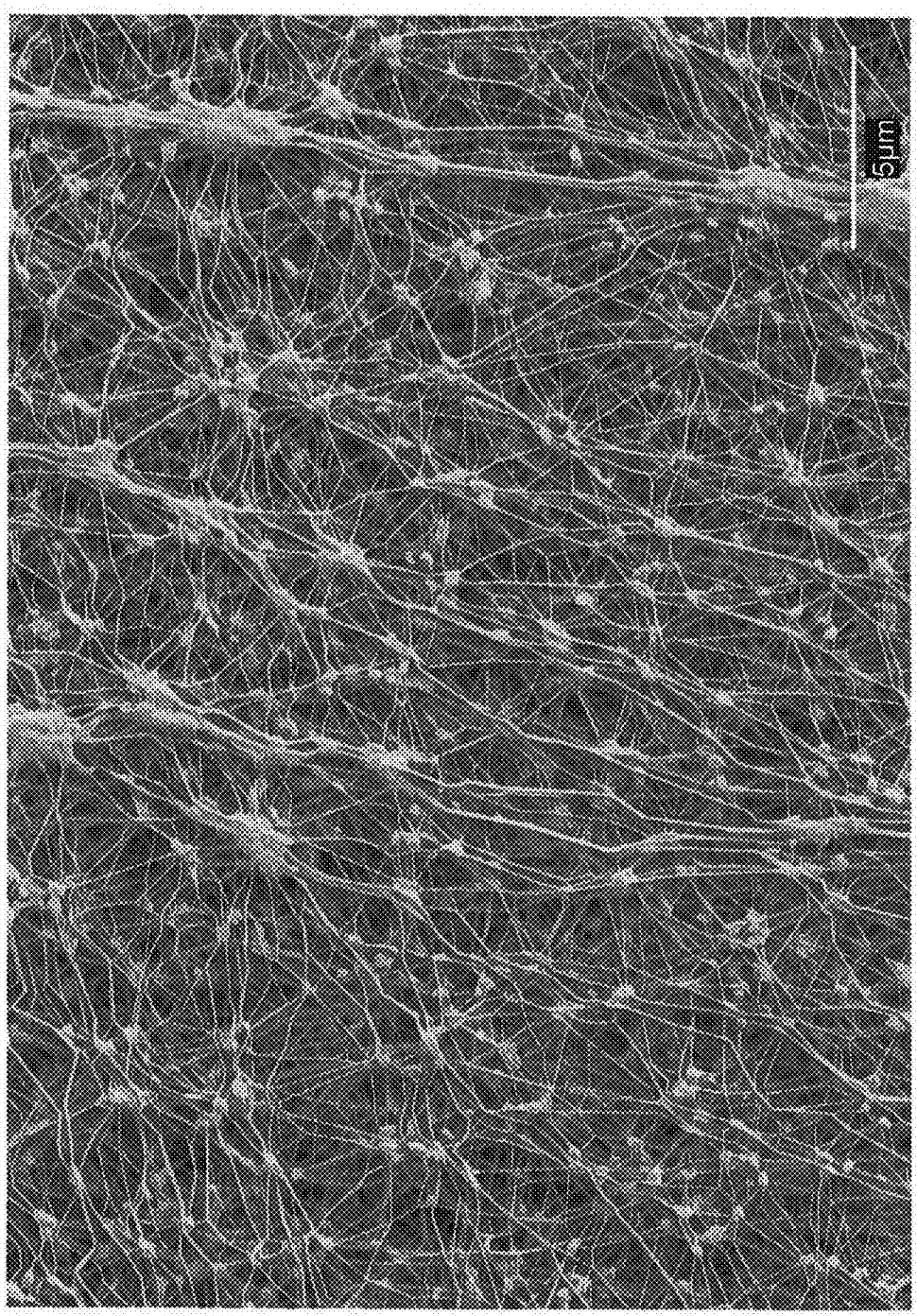
FIGS. 7A, 7B and 7C are scanning electron micrograph images of expanded fluoropolymer membranes used to form the valve leaflets, in accordance with an embodiment.

The expanded fluoropolymer in accordance with some embodiments, may comprise any suitable microstructure for achieving the desired leaflet performance. In one embodiment, the expanded fluoropolymer may comprise a microstructure of nodes interconnected by fibrils, such as described in U.S. Pat. No. 3,953,566 to Gore. In one embodiment, the microstructure of an expanded fluoropolymer membrane comprises nodes interconnected by fibrils as shown in the scanning electron micrograph image in FIG. 7A. The fibrils extend from the nodes in a plurality of directions, and the membrane has a generally homogeneous structure. Membranes having this microstructure may exhibit a ratio of matrix tensile strength in two orthogonal directions of less than about 2, and possibly less than about 1.5.

Figure 7B:
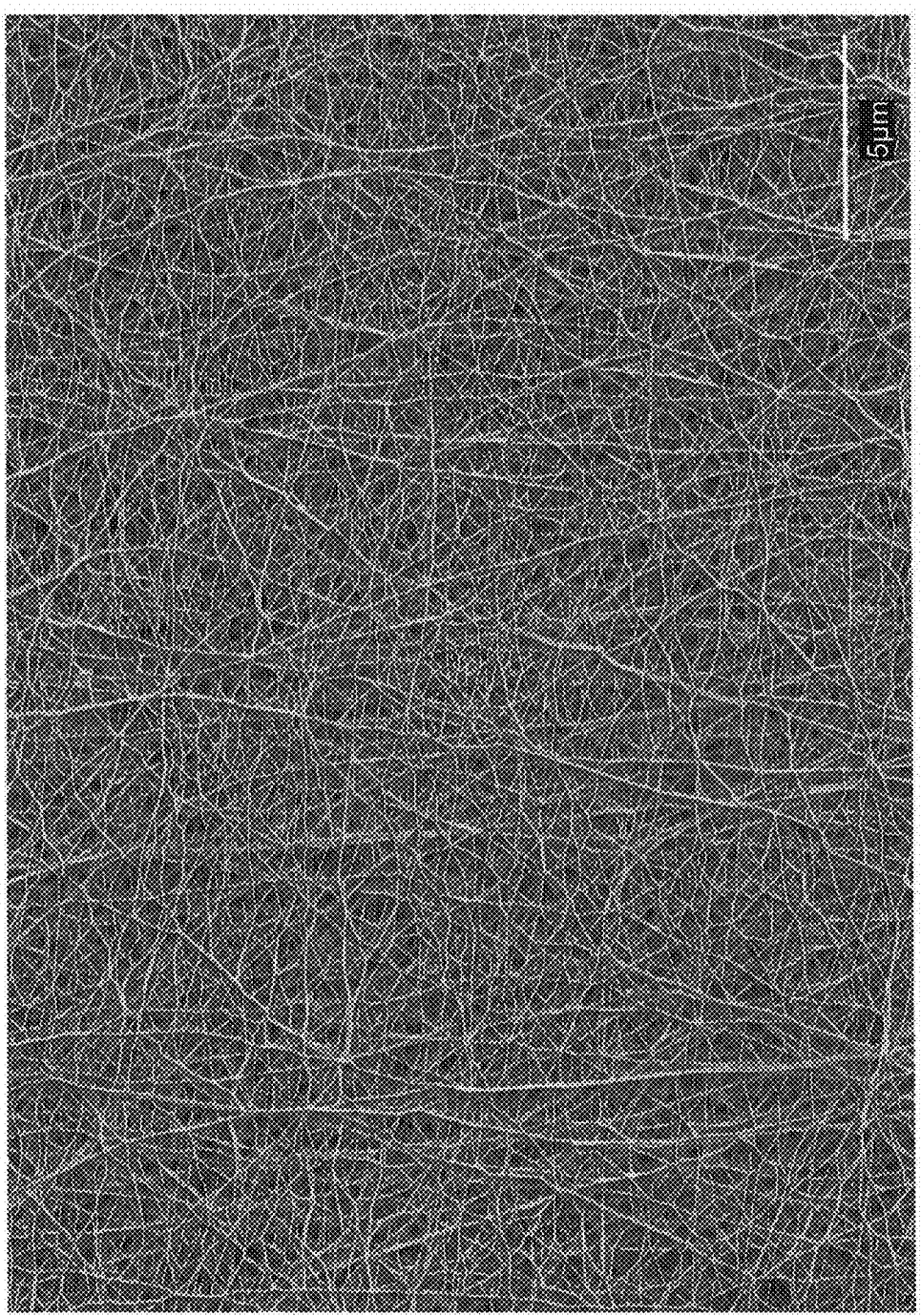
Figure 7C:
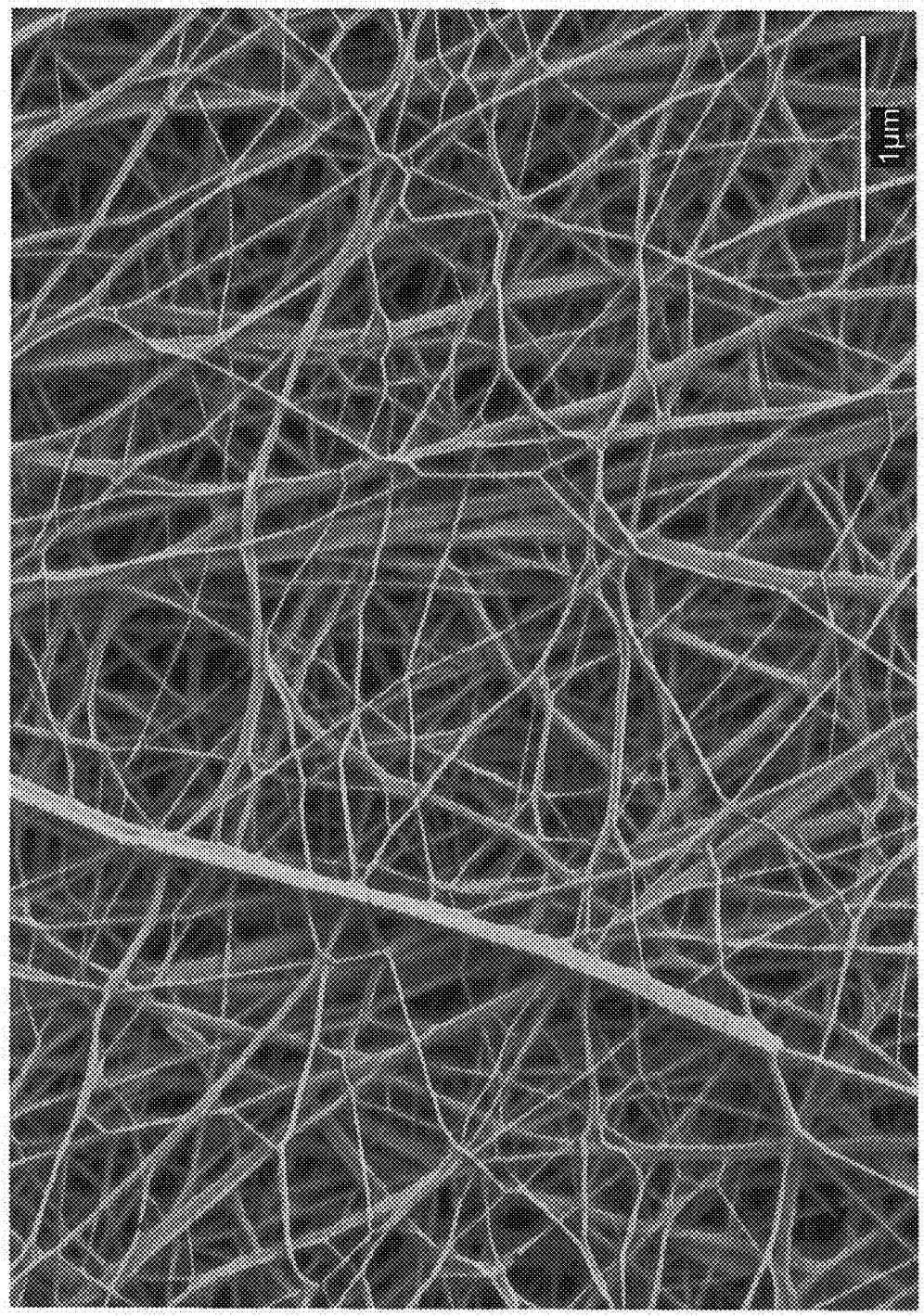

In another embodiment, the expanded fluoropolymer may have a microstructure of substantially only fibrils, such as, for example, depicted in FIGS. 7B and 7C, as is generally taught by U.S. Pat. No. 7,306,729, to Bacino. FIG. 7C is a higher magnification of the expanded fluoropolymer membrane shown in FIG. 7B, and more clearly shows the homogeneous microstructure having substantially only fibrils. The expanded fluoropolymer membrane having substantially only fibrils as depicted in FIGS. 7B and 7C, may possess a high surface area, such as greater than about 20 $m^2/g$, or greater than about 25 $m^2/g$, and in some embodiments may provide a highly balanced strength material having a product of matrix tensile strengths in two orthogonal directions of at least $1.5 \times 10^5$ $MPa^2$, and/or a ratio of matrix tensile strengths in two orthogonal directions of less than about 2, and possibly less than about 1.5. It is anticipated that expanded fluoropolymer membrane may have a mean flow pore sizes of less than about 5 µm, less than about 1 µm, and less than about 0.10 µm, in accordance with embodiments.

The expanded fluoropolymer in accordance with some embodiments may be tailored to have any suitable thickness and mass to achieve the desired leaflet performance. In some cases, it may be desirable to use a very thin expanded fluoropolymer membrane having a thickness less than about 1.0 µm. In other embodiments, it may be desirable to use an expanded fluoropolymer membrane having a thickness greater than about 0.1 µm and less than about 20 µm. The expanded fluoropolymer membranes can possess a specific mass less than about 1 $g/m^2$ to greater than about 50 $g/m^2$.

Membranes comprising expanded fluoropolymer according to an embodiment can have matrix tensile strengths ranging from about 50 MPa to about 400 MPa or greater, based on a density of about 2.2 $g/cm^3$ for PTFE.

Additional materials may be incorporated into the pores or within the material of the membranes or in between the layers of the membranes to enhance desired properties of the leaflet. Composites according to one embodiment can include fluoropolymer membranes having thicknesses ranging from about 500 µm to less than about 0.3 µm.

Embodiments of expanded fluoropolymer membrane combined with elastomer provides performance attributes required for use in high-cycle flexural implant applications, such as heart valve leaflets, in at least several significant ways. For example, the addition of the elastomer improves the fatigue performance of the leaflet by eliminating or reducing the stiffening observed with ePTFE-only materials. In addition, it reduces the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in substantially all of the pores of the at least one fluoropolymer layer. Having elastomer filling the pore volume or present in substantially all of the pores reduces the space in which foreign materials can be undesirably incorporated into the composite. An example of such foreign material is calcium. If calcium becomes incorporated into the composite material, as used in a heart valve leaflet, for example, mechanical damage can occur during cycling, thus leading to the formation of holes in the leaflet and degradation in hemodynamics.

In one embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675. As discussed above, the elastomer is combined with the expanded fluoropolymer membrane such that the elastomer occupies substantially all of the void space or pores within the expanded fluoropolymer membrane. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In another embodiment, a method of filling the pores of the expanded fluoropolymer membrane includes the steps of delivering the filler via a dispersion to partially or fully fill the pores of the expanded fluoropolymer membrane;

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675, and other references that would be known to those of skill in the art. For instance, in another embodiment shown in Example 1, a leaflet was formed from a composite of 53% by weight of elastomer to ePTFE and was subjected to cycle testing. Some stiffening was observed by around 200 million test cycles, though with only modest effect on hydrodynamics. When the weight percent of elastomer was raised to about 83% by weight, as in the embodiment of Example 2, no stiffening or negative changes in hydrodynamics were observed at about 200 million cycles. In contrast, with non-composite leaflets, i.e. all ePTFE with no elastomer, as in the Comparative Example B, severe stiffening was apparent by 40 million test cycles. As demonstrated by these examples, the durability of porous fluoropolymer members can be significantly increased by adding a relatively high-percentage of relatively lower strength elastomer to the pores of the fluoropolymer members. The high material strength of the fluoropolymer membranes also permits specific configurations to be very thin.

Other biocompatible polymers which may be suitable for use may include, but not be limited to, the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

In addition to expanded fluoropolymer, other biocompatible synthetic polymers may be suitable for use as a porous membrane. As provided below, embodiments comprising microporous polyethylene are provided as a biocompatible polymer suitable for the particular purpose.

An embodiment of a microporous polyethylene membrane includes a sheet of material comprising substantially all fibers having a diameter of less than about 1 μm. In another embodiment of a microporous polyethylene membrane includes a sheet of non-woven material comprising substantially all fibers having a diameter of less than about 1 μm. In some cases, it may be desirable to use a very thin microporous polyethylene membrane having a thickness less than about 10.0 μm. In other embodiments, it may be desirable to use a microporous polyethylene membrane having a thickness less than about 0.6 μm.

It is appreciated that the structure of the microporous membranes disclosed in embodiments provided herein, may be differentiated from other structures such as fabrics, knits and fiber windings, by looking at the specific surface area of the material. Embodiments of microporous membranes provided herein have a specific surface area of greater than about 4.0 $m^2/cc$. In accordance with other embodiments of microporous membranes provided herein have a specific surface area of greater than about 10.0 $m^2/cc$. The embodiments provided herein appreciate that a membrane having a specific surface area of greater than about 4.0 to more than about 60 $m^2/cc$ provide a significant improvement to, at least, but not limited to, the durability and lifetime of the heart valve when used as leaflet material.

It is appreciated that microporous membranes disclosed in embodiments provided herein may alternatively be differentiated from other structures such as fabrics, knits and fiber windings, by looking at the fiber diameter of the material. Embodiments of microporous membranes provided herein contain a majority of fibers having a diameter that is less than about 1 μm. Other embodiments of microporous membranes provided herein contain a majority of fibers having a diameter that is less than about 0.1 μm. The embodiments provided herein recognize that a membrane comprising fibers the majority of which are less than about 1 to beyond less than about 0.1 μm provide a significant improvement to, at least, but not limited to, the durability and lifetime of the heart valve when used as leaflet material.

Figure 30B:
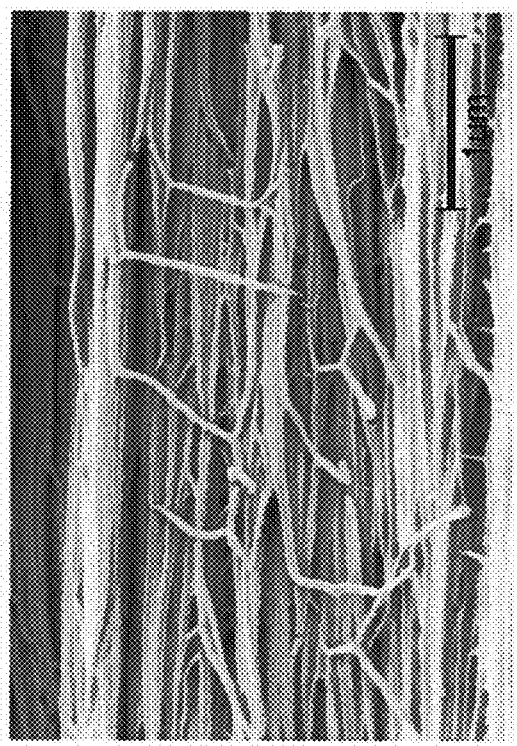
FIG. 30B is a scanning electron micrograph image of a cross-section of the microporous polyethylene membrane of FIG. 30B, in accordance with an embodiment.
Figure 30A:
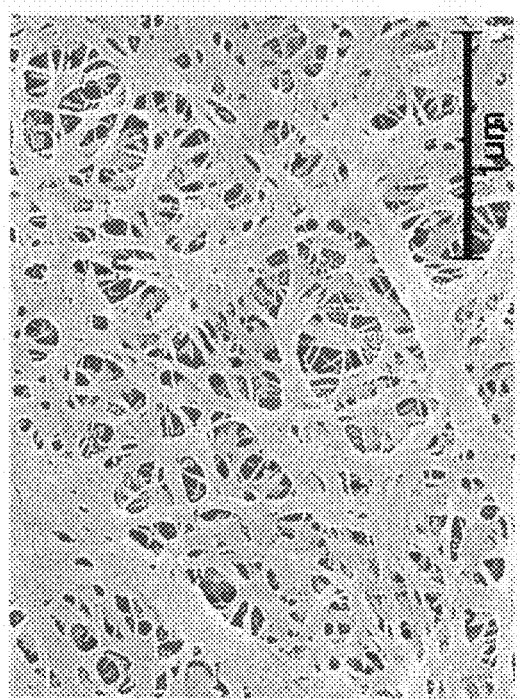
FIG. 30A is a scanning electron micrograph image of the surface of the microporous polyethylene membrane used to form the valve leaflets, in accordance with an embodiment.

The microporous polymer membranes of embodiments may comprise any suitable microstructure and polymer for achieving the desired leaflet performance. In some embodiments, the microporous polymer membrane is porous polyethylene that has a microstructure of substantially only fibers, such as, for example, depicted in FIGS. 30A and 30B for the material included in Example 4 and FIGS. 31A and 31B for the material included in Example 5. FIG. 30 shows a substantially homogeneous microstructure of the porous polyethylene membrane having substantially only fibers having a diameter of less than about 1 μm. The porous polyethylene membrane had a thickness of 0.010 mm, a porosity of 31.7%, a mass/area of 6.42 $g/m^2$, and a specific surface area of 28.7 $m^2/cc$.

Figure 31B:
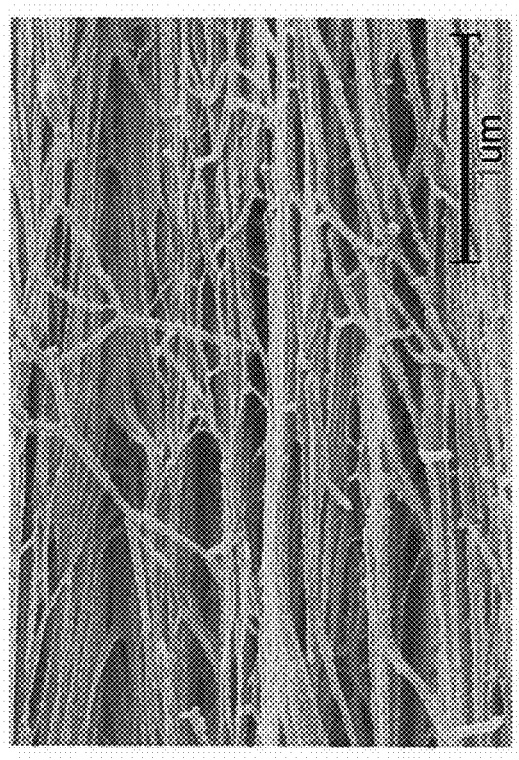
FIG. 31B is a scanning electron micrograph image of a cross-section of the microporous polyethylene membrane of FIG. 31B, in accordance with an embodiment.
Figure 31A:
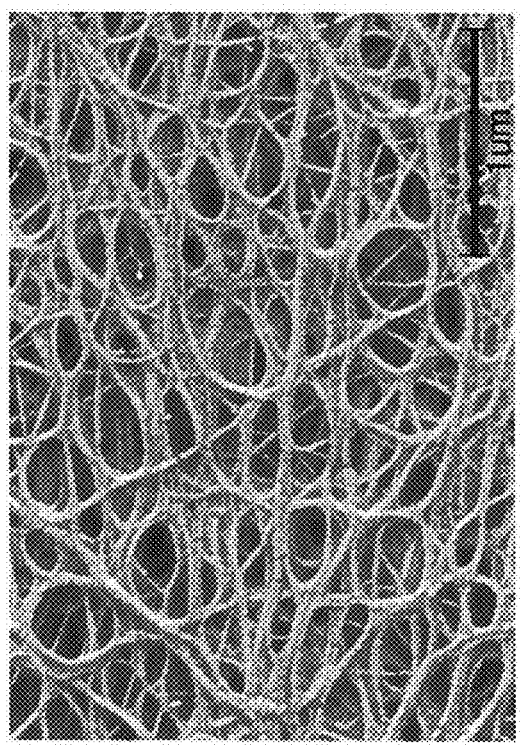
FIG. 31A is a scanning electron micrograph image of stretched microporous polyethylene membrane used to form the valve leaflets, in accordance with an embodiment.

FIGS. 31A and 31B, a surface and cross-sectional view, respectively, is the same porous polyethylene membrane shown in FIGS. 30A and 30B, a surface and cross-sectional view, respectively, that has been stretched in accordance with a process described below for Example 5. The stretched polyethylene membrane retains a substantially homogeneous microstructure having substantially only fibers having a diameter of less than about 1 μm. The stretched polyethylene membrane had a thickness of 0.006 mm, a porosity of 44.3%, a mass/area of 3.14 $g/m^2$, and a specific surface area of 18.3 $m^2/cc$. It is anticipated that microporous polyethylene membrane may have a mean flow pore sizes of less than about 5 μm, less than about 1 μm, and less than about 0.10 μm, in accordance with embodiments.

The following non-limiting examples are provided to further illustrate various embodiments.

Example 1

In accordance with an embodiment, heart valve leaflets were formed from a composite material having an expanded fluoropolymer membrane and an elastomeric material and joined to a metallic balloon expandable stent, as described by the following embodiment of a process:

A thick, sacrificial tooling cushion pad or layer was formed by folding a ePTFE layer over upon itself to create a total of four layers. The ePTFE layer was about 5 cm (2") wide, about 0.5 mm (0.02") thick and had a high degree of compressibility, forming a cushion pad. Referring to FIGS. 1 and 2, the cushion pad 200 was then stretched (FIG. 2) onto a leaflet tool, generally indicated at 100. The leaflet tool 100 has a leaflet portion 102, a body portion 104 and a bottom end 106. The leaflet portion 102 of the leaflet tool 100 has a generally arcuate, convex end surface 103. The cushion pad 200 was stretched and smoothed over the end surface 103 of the leaflet portion 102 of the leaflet tool 100 by forcing the leaflet tool 100 in the direction depicted by the arrow (FIG. 2A). A peripheral edge 202 of the cushion pad 200 was stretched over the bottom end 106 of the leaflet tool 100 and twisted to hold the cushion pad 200 in place (FIG. 2B).

Figure 2B:
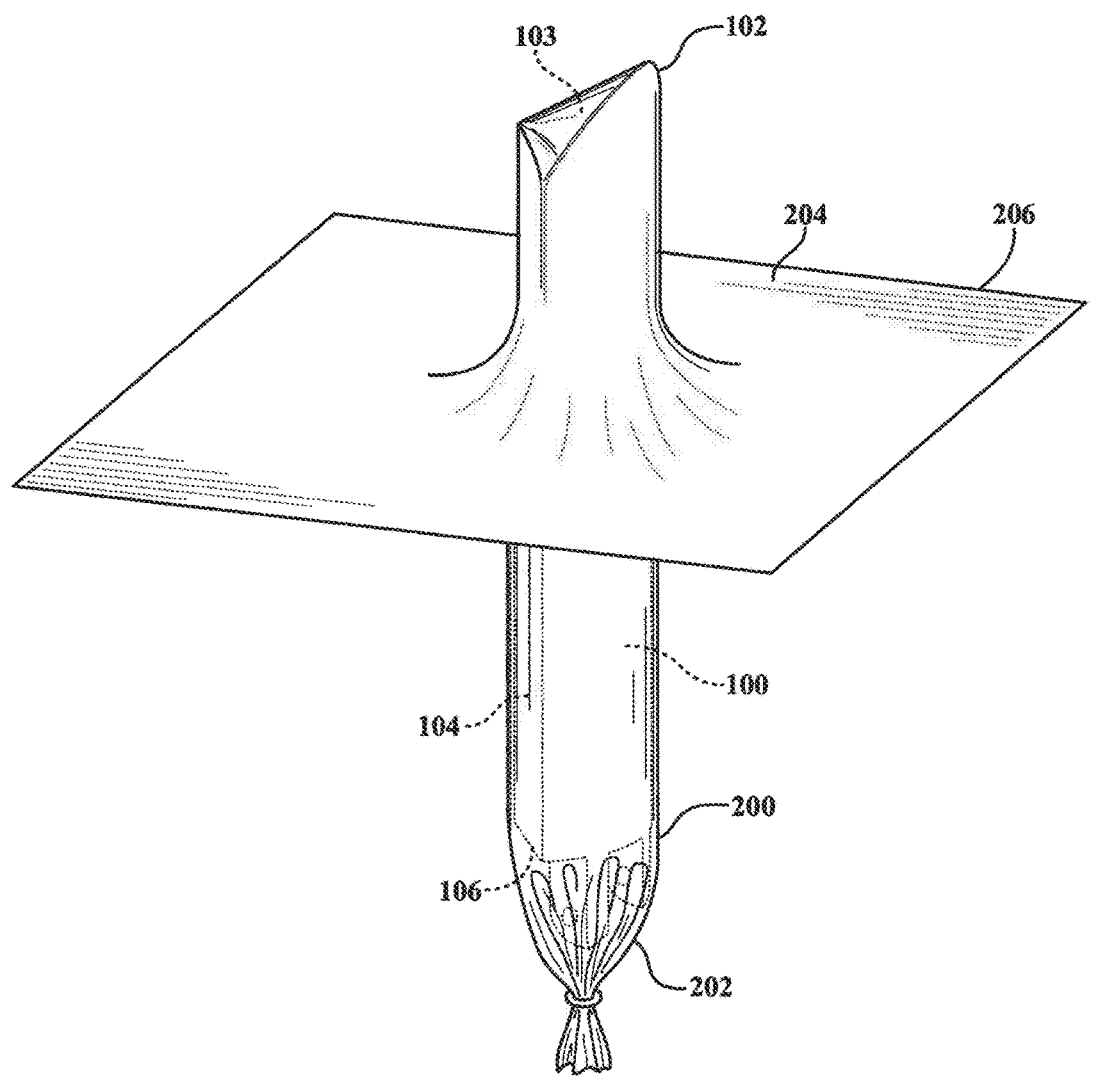
FIG. 2B is a perspective view of a release layer being stretched over the cushion pad covered leaflet tool in FIG. 2A, in accordance with an embodiment.

Referring to FIG. 2B, a release layer 204 was then stretched over the leaflet portion 102 of the leaflet tool 100 which in the previous step was covered with the cushion pad 200. In one embodiment, the release layer 204 was made from a substantially nonporous ePTFE having a layer of fluorinated ethylene propylene (FEP) disposed along an outer surface or side thereof. The release layer 204 was stretched over the leaflet tool 100 such that the FEP layer faced toward the cushion pad 200 and the substantially nonporous ePTFE faced outwardly or away from the cushion pad 200. The release layer was about 25 μm thick and of sufficient length and width to allow the release layer 204 to be pulled over the bottom end 106 of the leaflet tool 100. As with the cushion pad 200 in the previous step, a peripheral edge 206 of the release layer 204 was pulled toward the bottom end 106 of the leaflet tool 100 and then twisted onto the bottom end 106 of the leaflet tool 100 to retain or hold the release layer 204 in place. The FEP layer of the release layer 204 was then spot-melted and thereby fixedly secured to the cushion pad 200, as required, by the use of a hot soldering iron.

The processes of Steps 1) and 2) were repeated to prepare three separate leaflet tools, each having a cushion pad covered by a release layer.

A leaflet material according to one embodiment was formed from a composite material comprising a membrane of ePTFE imbibed with a fluoroelastomer. A piece of the composite material approximately 10 cm wide was wrapped onto a circular mandrel to form a tube. The composite material was comprised of three layers: two outer layers of ePTFE and an inner layer of a fluoroelastomer disposed therebetween. The ePTFE membrane was manufactured according to the general teachings described in U.S. Pat. No. 7,306,729. The fluoroelastomer was formulated according to the general teachings described in U.S. Pat. No. 7,462,675. Additional fluoroelastomers may be suitable and are described in U.S. Publication No. 2004/0024448.

The ePTFE membrane had the following properties: thickness=about 15 μm; MTS in the highest strength direction=about 400 MPa; MTS strength in the orthogonal direction=about 250 MPa; Density=about 0.34 g/cm$^3$; IBP=about 660 KPa.

The copolymer consists essentially of between about 65 and 70 weight percent perfluoromethyl vinyl ether and complementally about 35 and 30 weight percent tetrafluoroethylene.

The percent weight of the fluoroelastomer relative to the ePTFE was about 53%.

The multi-layered composite had the following properties: thickness of about 40 μm; density of about 1.2 g/cm$^3$; force to break/width in the highest strength direction=about 0.953 kg/cm; tensile strength in the highest strength direction=about 23.5 MPa (3,400 psi); force to break/width in the orthogonal direction=about 0.87 kg/cm; tensile strength in the orthogonal direction=about 21.4 MPa (3100 psi), IPA bubble point greater than about 12.3 MPa, Gurley Number greater than about 1,800 seconds, and mass/area=about 14 g/m$^2$.

The following test methods were used to characterize the ePTFE layers and the multi-layered composite.

The thickness was measured with a Mutitoyo Snap Gage Absolute, 12.7 mm (0.50") diameter foot, Model ID-C112E, Serial #10299, made in Japan. The density was determined by a weight/volume calculation using an Analytical Balance Mettler PM400 New Jersey, USA. The force to break and tensile strengths were measured using an Instron Model #5500R Norwood, Mass., load cell 50 kg, gage length=25.4 cm, crosshead speed=25 mm/minute (strain rate=100% per minute) with flat faced jaws. The IPA Bubble Point was measured by an IPA bubble point tester, Pressure Regulator Industrial Data Systems Model LG-APOK, Salt Lake City, Utah, USA, with a Ramp Rate of 1.38 KPa/s (0.2 psi/s), 3.14 cm$^2$ test area. The Gurley Number was determined as the time in seconds for 100 cm$^3$ of air to flow through a 6.45 cm$^2$ sample at 124 mm of water pressure using a Gurley Tester, Model #4110, Troy, N.Y., USA.

Unless otherwise noted, these test methods were used to generate the data in subsequent examples.

Layers of the composite material, each having two outer layers of ePTFE and an inner layer of a fluoroelastomer disposed therebetween, was wrapped onto a mandrel having a diameter of about 28 mm (1.1") such that the higher strength direction of the membrane was oriented in the axial direction of the mandrel. In one embodiment, four layers of the composite material were wrapped in a non-helical, generally circumferential fashion onto the mandrel. The composite material had a slight degree of tackiness that allowed the material to adhere to itself. While still on the mandrel, the composite material was slit longitudinally generally along the mandrel long axis to form a sheet about 10 cm (4") by about 90 mm (3.5").

The resulting sheet of leaflet material (or composite material from Step 4) was then cut and wrapped onto the leaflet tool 100 having a cushion pad 200 covered by a release layer 204. More specifically, as shown in FIGS. 3A-3C, the leaflet material 300 was placed onto a flat cutting surface. The leaflet tool 100 with the cushion pad 200 and release layer 204 was then aligned onto the leaflet material 300 approximately as shown. Four slits 302, 304, 306, 308 were then formed in the leaflet material 300 with a razor blade. One pair of slits 302, 304 extends from one side of the leaflet tool 100 and terminates at one edge 300a of the leaflet material 300, and the other pair of slits 306, 308 extends from an opposite side of the leaflet tool 100 and terminates at an opposite edge 300b of the leaflet material 300. The slits 302, 304, 306, 308 were spaced apart from the leaflet portion 102 of the leaflet tool 100. The slits 302, 304, 306, 308 did not protrude under the leaflet tool 100. It should be appreciated that the widths of the individual slits are shown not to scale. The slits 302, 304, 306, 308 in the leaflet material 300 resulted in the formation of a folding portion 310, a pair of straps 312, 314 and excess material of leaflet material 315. The folding portions 310 were then folded in the general direction indicated by the arrows 316 in FIG. 3C and smoothed over the leaflet tool 100, which was covered by the cushion pad 200 and the release layer 204 in the previous steps.

The leaflet material 315 was then stretched and smoothed over the leaflet portion 102, particularly the end surface 103 of the leaflet tool 100. The Steps 4) and 5) were repeated to form three separate leaflet assemblies. The three leaflet assemblies 402, 404, 406 were then clamped together to form a tri-leaflet assembly 400, as shown in FIG. 4. Shown are the three separate leaflet assemblies 402, 404, 406, each having an excess material of leaflet material 315 extending generally radially beyond the periphery of the tri-leaflet assembly 400.

Figures 5A, 5B:
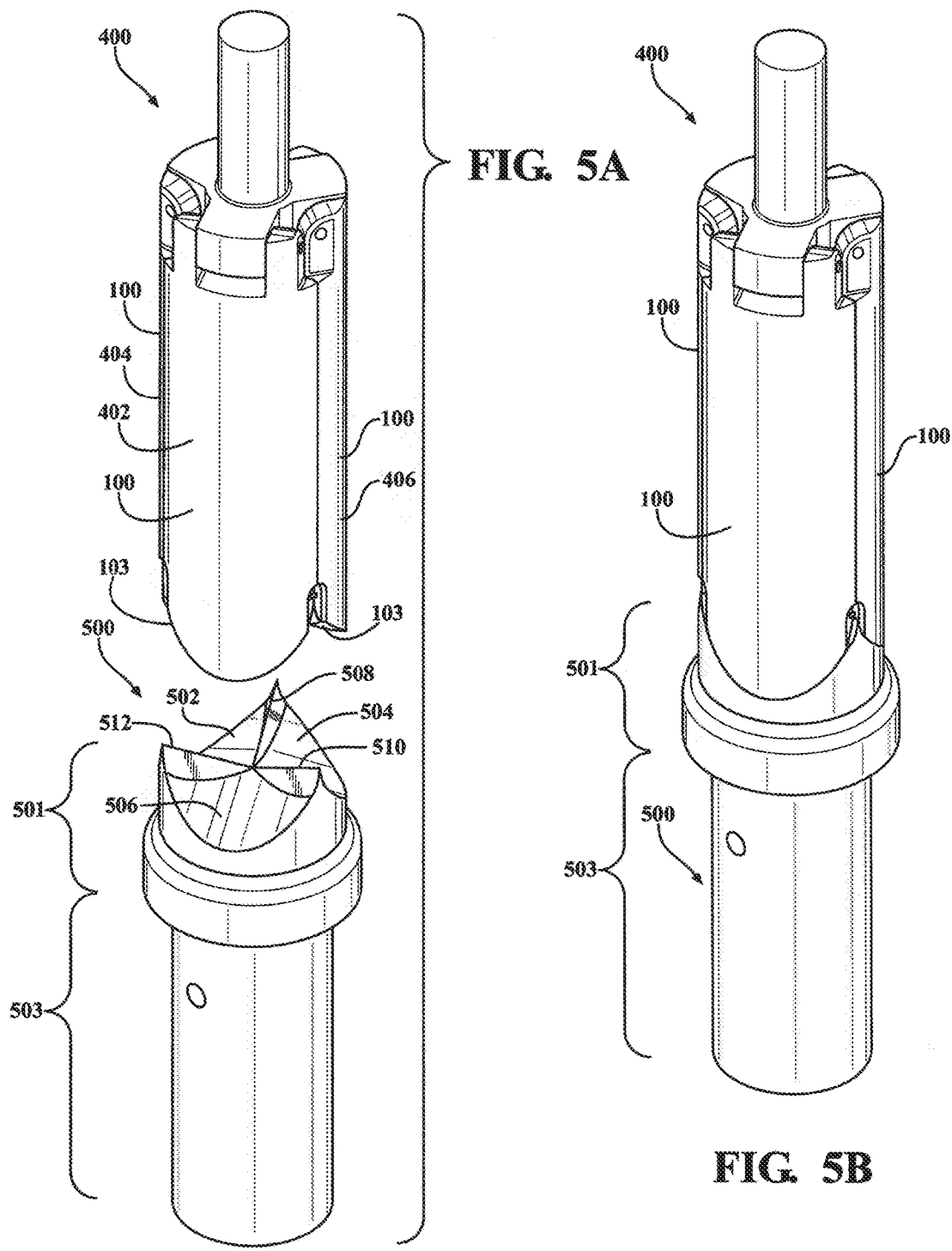
FIG. 5A is a perspective view of the tri-leaflet assembly and a base tool, in accordance with an embodiment.
FIG. 5B is a perspective view of the tri-leaflet assembly and base tool aligned and assembled to form a base tool assembly, in accordance with an embodiment.

A base tool was then provided having cavities for engaging the end surfaces of the leaflet tools of the tri-leaflet assembly and trimming the excess leaflet area to form three leaflets. Referring to FIG. 5A, the base tool is generally indicated at 500 and extends longitudinally between an end 501 and an opposite bottom end 503. Three concave cavities 502, 504, 506 are formed in the end 501 of the base tool 500. Each concave cavity 502, 504, 506 is formed to match fit or nestingly seat the end surface 103 of one of the three leaflet assemblies 402, 404, 406. Three radially extending elements 508, 510, 512 extend outwardly from the end of the base tool 500. Each element 508, 510, 512 is disposed between an adjacent pair of concave cavities 502, 504, 506.

The base tool 500 was then prepared having a compression pad and a release layer (not shown) similar to how the leaflet tool was prepared in Steps 1 and 2. As described for each leaflet tool in Steps 1 and 2, the compression pad and the release layer were similarly stretched and affixed to the base tool 500 to form a base tool assembly.

Referring to FIG. 5B, the base tool assembly (illustrated for convenience as the base tool 500 without showing the cushion pad and the release layer) and the tri-leaflet assembly, generally indicated at 400, were then generally axially aligned together so that the end surface (not shown) of each leaflet tool 100 was seated into one of the concave cavities (not shown) in the end 501 of the base tool, generally indicated at 500, to form a combined tool assembly.

A metallic balloon expandable stent was then fabricated. A tube of 316 stainless steel having a wall thickness of about 0.5 mm (0.020") and a diameter of about 2.5 cm (1.0") was laser cut. A pattern was cut into the tube to form an annular-shaped cut stent frame or support structure, which is generally indicated at 600 and shown illustratively in a flat, plane view in FIG. 6a. The support structure 600, includes a plurality of small closed cells 602, a plurality of large closed cells 604, and a plurality of leaflet closed cells 606. Note that one of the plurality of leaflet closed cells 606 appears as an open cell in FIG. 6A due to the flat plane view. The cells 602, 604, 606 are generally arranged along rows forming the annular shape of the support structure 600.

Polymeric materials were then adhered to the laser cut stent frame. First, a sacrificial compression layer of ePTFE membrane was wrapped without overlap onto a mandrel (not shown) having a diameter of about 2.5 cm (1.0"). The sacrificial compression layer of ePTFE membrane had a thickness of about 0.5 mm (0.02") and a width of about 10 cm (4"), and was compliant and compressible to provide a soft, sacrificial compression layer.

Four layers of a substantially nonporous, ePTFE film were then wrapped onto the mandrel on top of the compression layer membrane. The substantially nonporous, ePTFE film had a thickness of about 25 μm (0.001"), was about 10 cm (4") wide and had a layer of FEP on one side. The substantially nonporous, ePTFE film was wrapped with the FEP facing away from the mandrel. The substantially nonporous, ePTFE film had the properties of the release layer previously described in Step 2).

A thin film of type 1 (ASTM D3368) FEP was constructed using melt extrusion and stretching. An additional 10 layers of this type 1 (ASTM D3368) FEP film was added to the mandrel, which was previously wrapped in the compression layer membrane in Step 10 and the four layers of substantially nonporous, ePTFE film in Step 11. The type 1 (ASTM D3368) FEP film was about 40 μm (0.0016") thick and was about 7.7 cm (3") wide.

The wrapped mandrel was then heat treated in an air convection oven at about 320° C. for about 5 minutes and allowed to cool.

The support structure (indicated at 600 in FIG. 6A) was then placed onto the heat treated and wrapped mandrel. Two additional layers of type 1 (ASTM D3368) FEP film (provided in Step 12) were then wrapped onto the support structure, which was previously placed on the wrapped mandrel.

The wrapped mandrel and the support structure supported thereon were then heat treated in an air convection oven at about 320° C. for about 10 minutes and allowed to cool, forming a polymeric-coated support structure.

Figure 6A:
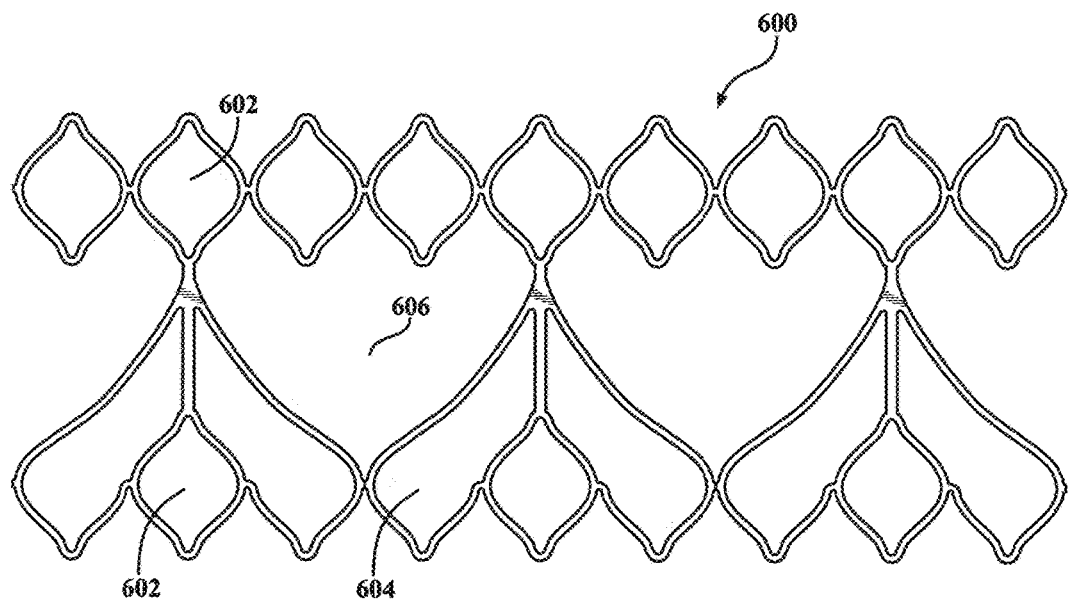
FIG. 6A is a flattened plane view of a stent frame or support structure, in accordance with an embodiment.
Figure 6B:
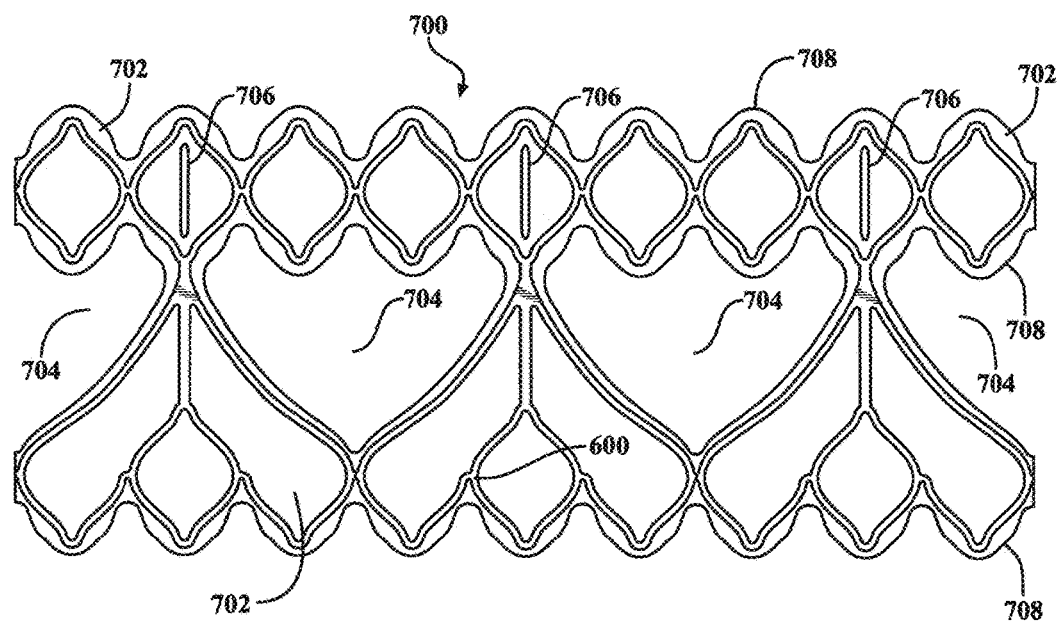
FIG. 6B is a flattened plane view of the support structure covered in a polymer coating, in accordance with an embodiment.

The polymeric-coated support structure was then trimmed with a scalpel to form a trimmed stent frame, which is generally indicated at 700 and shown illustratively in a flat, plane view in FIG. 6B. More specifically, in one manner, the polymeric coating was trimmed about 2 mm (0.08") past the edges of the support structure (600, FIG. 6A) to form a variety of edge profiles 708. In another manner, the polymeric coating was allowed to span entire cells to form a web in each cell. In either case, the support structure 600 was fully encapsulated within a polymeric coating 702 to form the trimmed stent frame 700. The trimmed stent frame 700 includes a plurality of leaflet openings 704 corresponding in number and generally in shape to the plurality of leaflet closed cells 606 (FIG. 6A). Further, a slit 706 is formed in the polymeric coating 702 of each of the small closed cells as shown in FIG. 6B. Specifically, each slit 706 is linear and generally parallel to a longitudinal center axis (not shown) of the annular-shaped support structure 600.

The trimmed stent frame was then placed onto the combined tool assembly from Step 8. The leaflet portions (102) of the leaflet tools were aligned to the leaflet openings (704 in FIG. 6B) in the trimmed stent frame. The three excess leaflet material areas (315 in FIG. 4) were pulled through the leaflet openings of the stent frame. Each of the three pairs of straps (312, 314 in FIG. 3A) was pulled through one of the slits (706 in FIG. 6B) and wrapped around the trimmed stent frame. Each pair of straps were wrapped in opposing directions relative to each other. The six straps were then heat tacked to the trimmed stent frame using a hot soldering iron.

The combined tool assembly (Step 8) and the trimmed stent frame having the wrapped and heat tacked straps were then mounted into a rotary chuck mechanism. The rotary chuck mechanism was then adjusted to apply a light, longitudinal compressive load. The excess leaflet material areas (315 in FIG. 4) were then heat tacked to the base tool (500 in FIG. 5) using a hot soldering iron.

The combined tools of Step 18 were then wrapped with an additional 2 layers of type 1 (ASTM D3368) FEP film (from Step 12). Three additional layers of the composite (Step 4) were then overwrapped and tacked down to the trimmed stent frame.

In preparation for a final heat treat, release and sacrificial layers of a compression tape and compression fiber were applied both circumferentially and longitudinally to the assembly from Step 19. The compression tape/fiber contact and compress the assembly both circumferentially and longitudinally during the subsequent heat treat. A sacrificial layer of compression tape was circumferentially wrapped in a helical fashion onto the assembly from Step 19. This compression tape had the properties of the sacrificial compression layer of ePTFE previously described in Step 10. An ePTFE compression fiber was then tightly wrapped onto the compression tape. Approximately 100 turns of the compression fiber were circumferentially applied in a closely spaced helical pattern. The ePTFE compression fiber was about 1 mm (0.04") in diameter and was structured to shrink longitudinally when sufficiently heated. The clamped assembly was then removed from the rotary chuck mechanism. Three layers of sacrificial compression tape were then wrapped in a longitudinal fashion around the assembly. Approximately 20 wraps of the compression fiber was then longitudinally wrapped over the longitudinal compression tape.

21). The assembly from Step 20 was then heat treated in an air convection oven at about 280° C. for about 90 minutes and then room temperature water quenched. This heat treatment step facilitates the flow of the thermoplastic fluoroelastomer into the pores of the ePTFE membrane used to create the leaflet material described in step 4.

Figure 8:
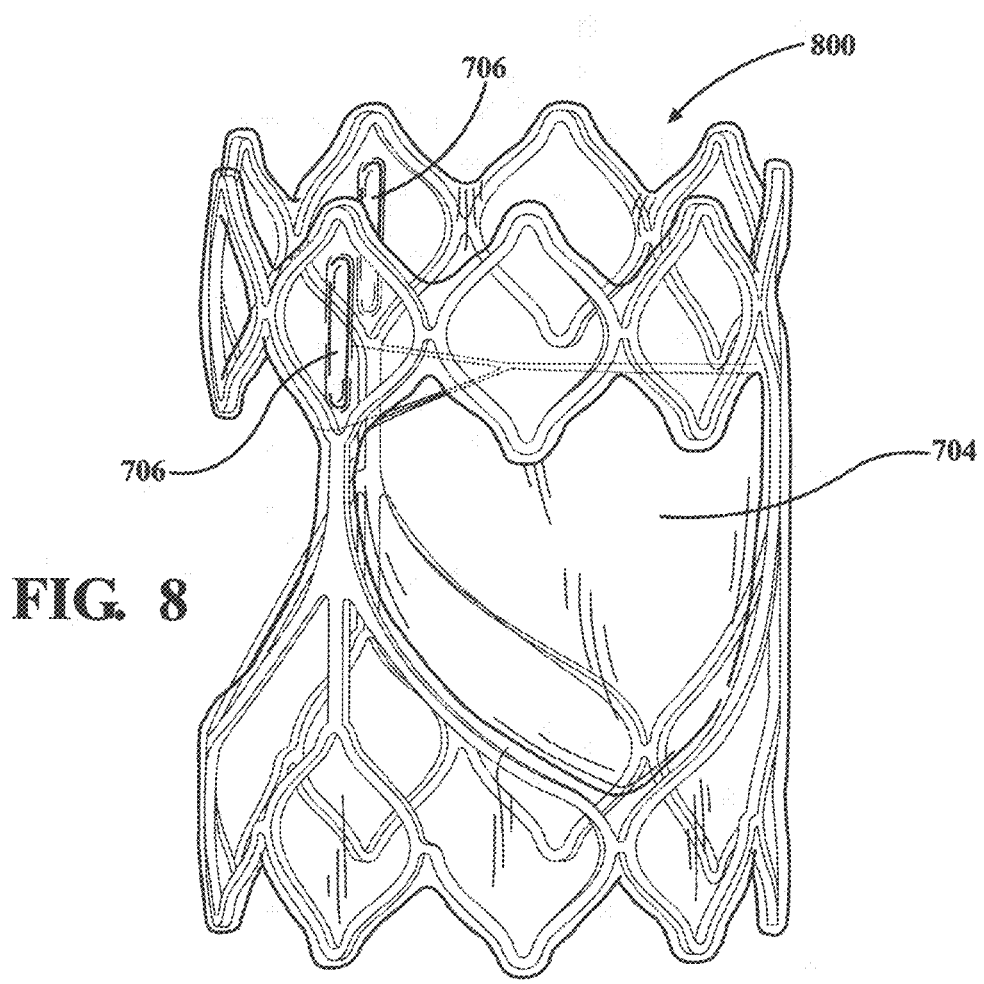
FIG. 8 is a perspective view of a valve assembly, in accordance with an embodiment.

The sacrificial compression tapes/fibers were then removed. The polymeric materials were trimmed to allow the leaflet and base tools to be separated. The stent polymeric layers were then trimmed to allow removal of the stent frame with the attached leaflets. The leaflets were then trimmed, resulting in a valve assembly as shown in FIG. 8 and generally indicated at 800.

Figure 9A:
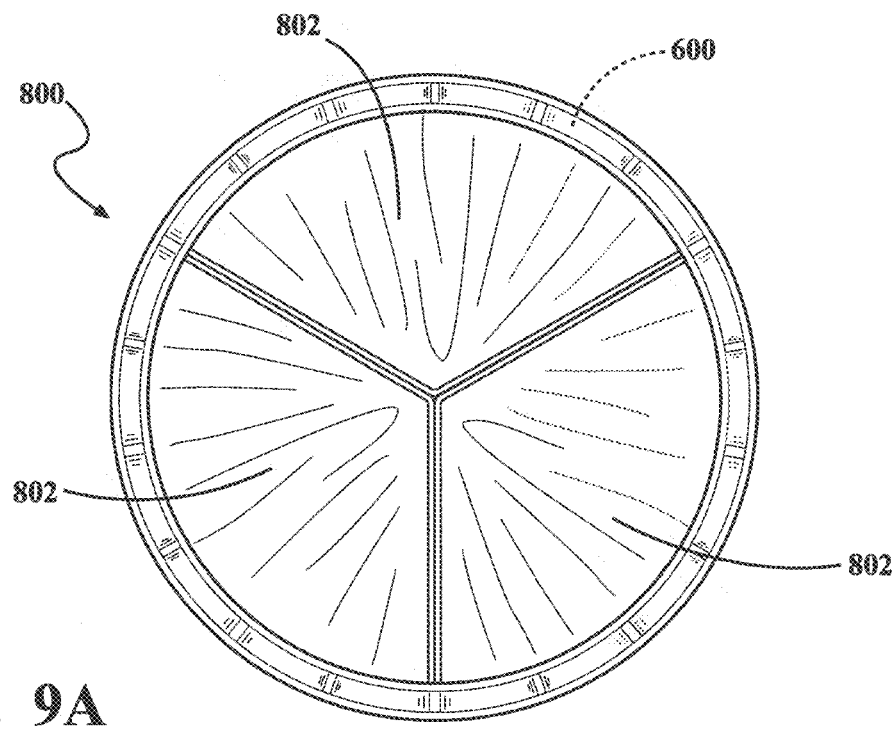
FIGS. 9A and 9B are top elevational views of the heart valve assembly of FIG. 8 shown illustratively in closed and open positions, respectively, in accordance with an embodiment.
Figure 9B:
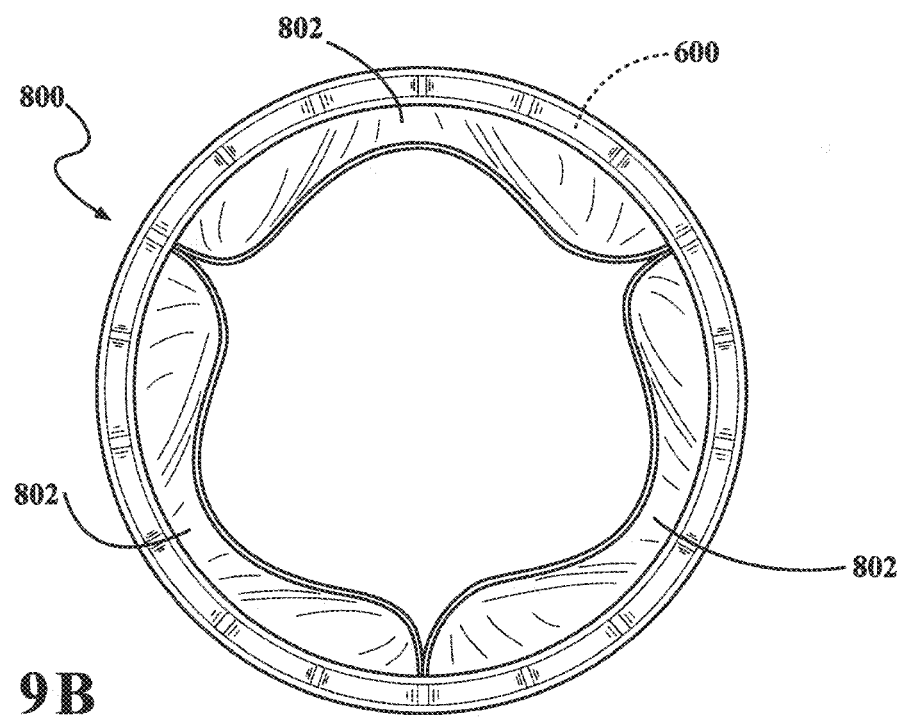

The resulting valve assembly 800, according to one embodiment, includes leaflets 802 formed from a composite material with at least one fluoropolymer layer having a plurality of pores and an elastomer present in substantially all of the pores of the at least one fluoropolymer layer. Each leaflet 802 is movable between a closed position, shown illustratively in FIG. 9A, in which blood is prevented from flowing through the valve assembly, and an open position, shown illustratively in FIG. 9B, in which blood is allowed to flow through the valve assembly. Thus, the leaflets 802 of the valve assembly 800 cycle between the closed and open positions generally to regulate blood flow direction in a human patient, The performance of the valve leaflets in each valve assembly was characterized on a real-time pulse duplicator that measured typical anatomical pressures and flows across the valve, generating an initial or "zero fatigue" set of data for that particular valve assembly. The valve assembly was then transferred to a high-rate fatigue tester and was subjected to approximately 207 million cycles. After each block of about 100 million cycles, the valve was then returned to the real-time pulse duplicator and the performance parameters re-measured.

The flow performance was characterized by the following process:

The valve assembly was potted into a silicone annular ring (support structure) to allow the valve assembly to be subsequently evaluated in a real-time pulse duplicator. The potting process was performed according to the recommendations of the pulse duplicator manufacturer (ViVitro Laboratories Inc., Victoria BC, Canada)

The potted valve assembly was then placed into a real-time left heart flow pulse duplicator system. The flow pulse duplicator system included the following components supplied by VSI Vivitro Systems Inc., Victoria BC, Canada: a Super Pump, Servo Power Amplifier Part Number SPA 3891; a Super Pump Head, Part Number SPH 5891B, 38.320 $cm^2$ cylinder area; a valve station/fixture; a Wave Form Generator, TriPack Part Number TP 2001; a Sensor Interface, Part Number VB 2004; a Sensor Amplifier Component, Part Number AM 9991; and a Square Wave Electro Magnetic Flow Meter, Carolina Medical Electronics Inc., East Bend, N.C., USA.

In general, the flow pulse duplicator system uses a fixed displacement, piston pump to produce a desired fluid flow through the valve under test.

The heart flow pulse duplicator system was adjusted to produce the desired flow, mean pressure, and simulated pulse rate. The valve under test was then cycled for about 5 to 20 minutes.

Figure 10:
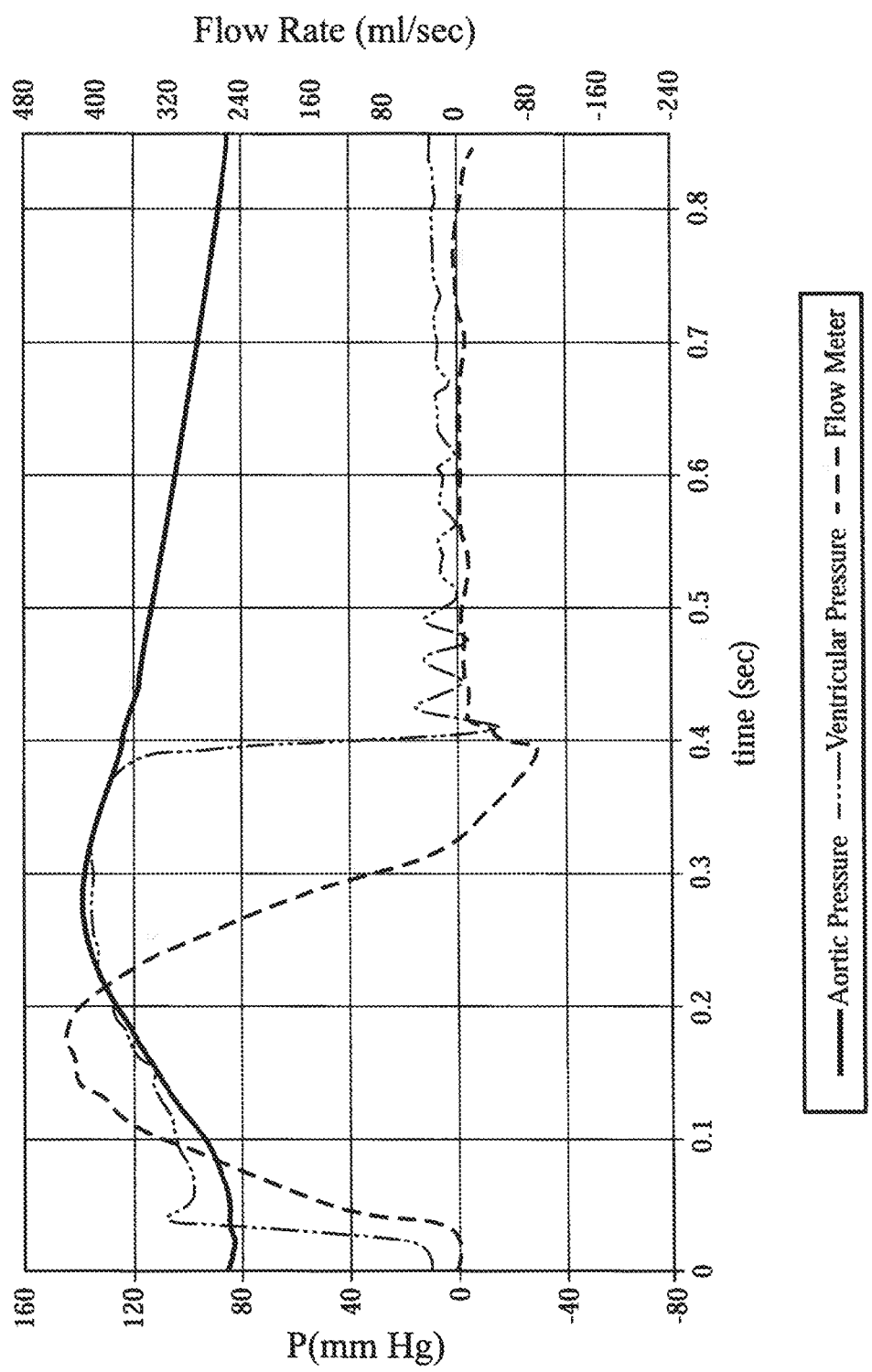
FIG. 10 is a graph of measured outputs from a heart flow pulse duplicator system used for measuring performance of the valve assemblies made in accordance with embodiments.

Pressure and flow data were measured and collected during the test period, including ventricular pressures, aortic pressures, flow rates, and pump piston position. FIG. 10 is a graph of data from the heart flow pulse duplicator system.

Parameters used to characterize the valve and to compare to post-fatigue values are pressure drop across the open valve during the positive pressure portion of forward flow, effective orifice area, and regurgitant fraction.

Figure 11A:
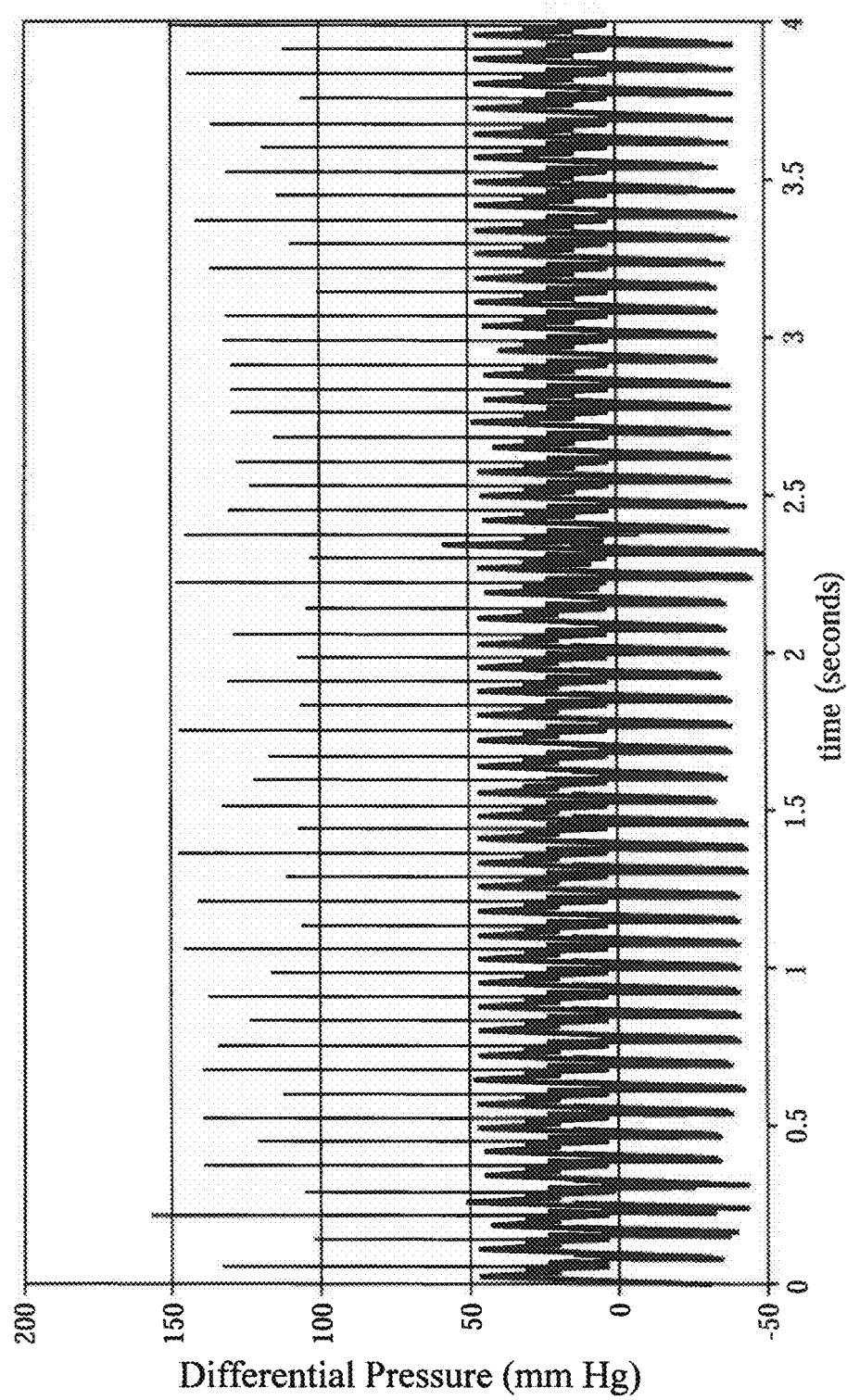

Following characterization, the valve assembly was then removed from the flow pulse duplicator system and placed into a high-rate fatigue tester. A Six Position Heart Valve Durability Tester, Part Number M6 was supplied by Dynatek, Galena, Mo., USA and was driven by a Dynatek Dalta DC 7000 Controller. This high rate fatigue tester displaces fluid through a valve assembly with a cycle rate of about 780 cycles per minute. During the test, the valve assembly can be visually examined using a tuned strobe light. The pressure drop across the closed valve can also be monitored as displayed in FIGS. 11A and 11B. Shown in FIGS. 11A and 11B is a data set verifying that the high-rate fatigue tester was producing consistent pressure waveforms.

The valve assembly was continuously cycled and periodically monitored for visual and pressure drop changes. After approximately 200 million cycles, the valve assembly was removed from the high-rate tester and returned to the real-time pulse duplicator. The pressure and flow data were collected and compared to the original data collected.

Figure 12A:
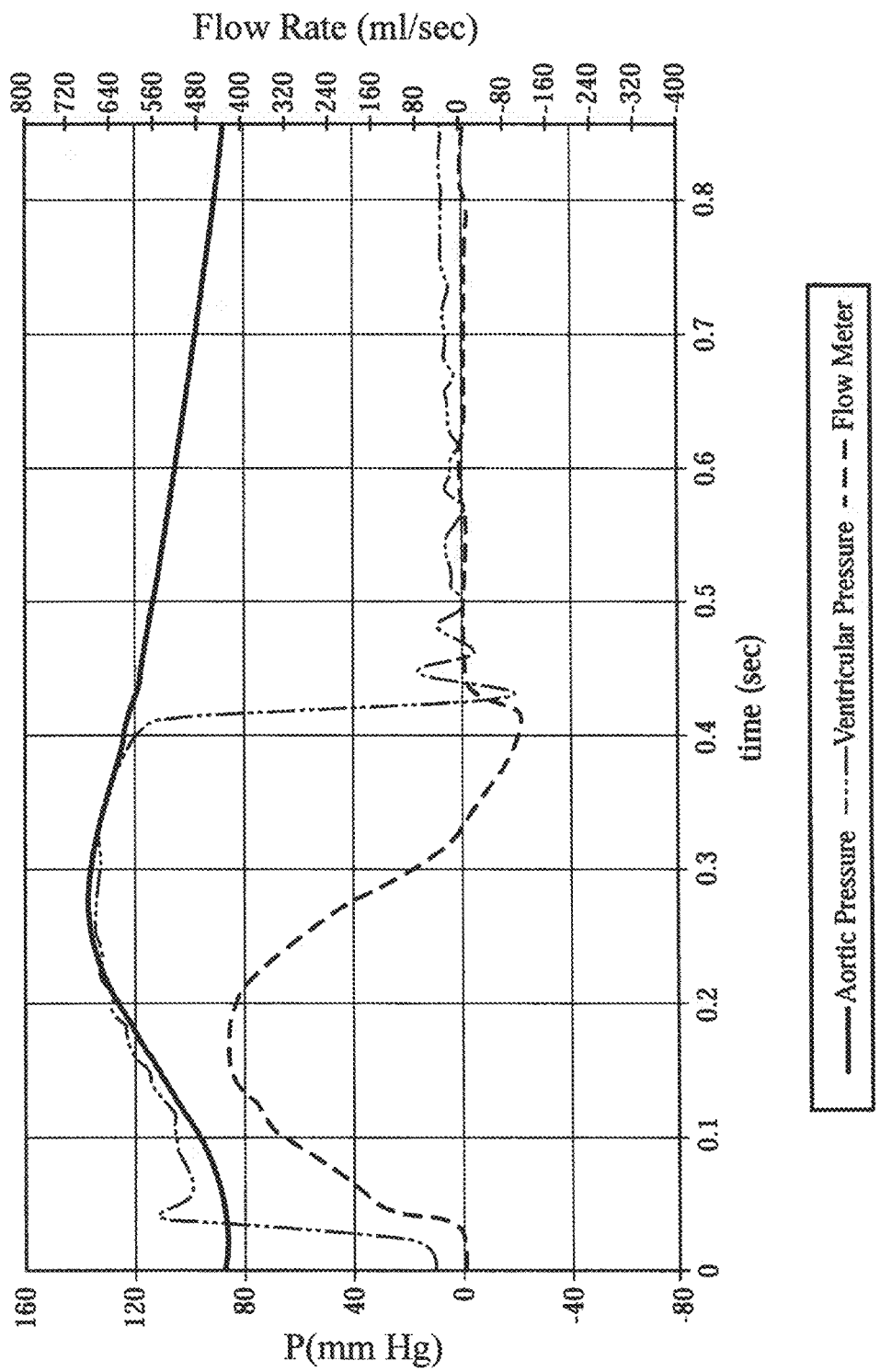
FIGS. 12A and 12B are graphs of measured outputs from the heart flow pulse duplicator system taken while testing valve assemblies according to embodiments at zero cycles and after about 207 million cycles, respectively.
Figure 12B:
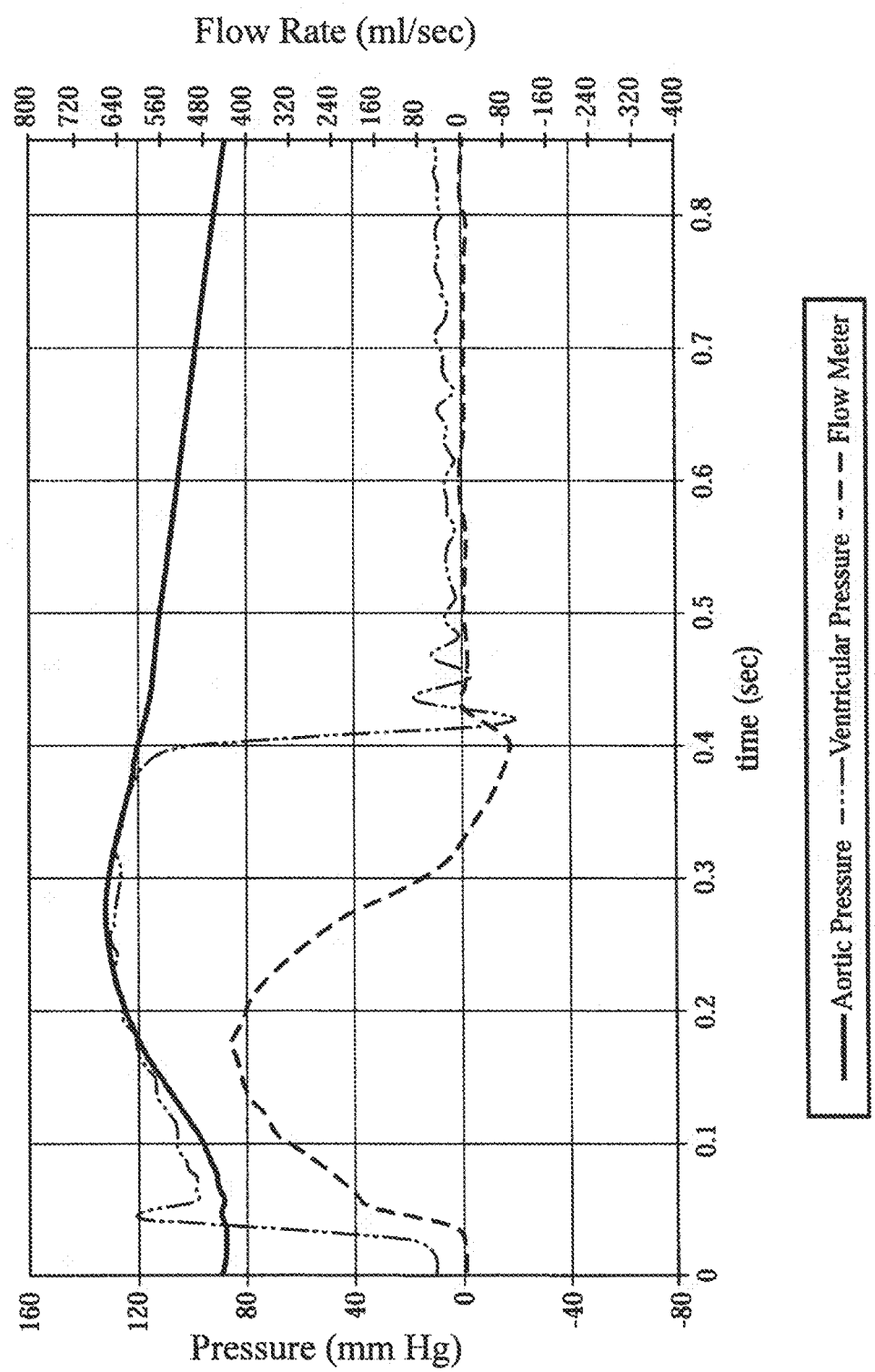

Shown in FIG. 12A is a screen shot displaying measured data output from the real-time heart flow pulse duplicator system. Shown are Ventricular Pressures, Aortic Pressures and Flow Rate. The initial or zero fatigue data for a particular valve is shown illustratively in FIG. 12A. The same measurements were taken and data were collected for the same particular valve after 207 million cycles. The 207 million cycle data for the particular valve is shown illustratively in FIG. 12B. Both sets of measurements were taken at 5 liters per minute flow rate and 70 cycles per minute rate. Comparing FIGS. 12A and 12B, it should be readily appreciated that the waveforms are substantially similar, indicating no substantial change in the valve leaflet performance after about 207 million cycles. Pressure drop, effective orifice area (EOA), and regurgitant fraction measured at zero and 207 million cycles are summarized in Table 1 below.

TABLE 1

| Number of cycles (Million) | Pressure Drop (mm Hg) | EOA (cm$^2$) | Regurgitant Fraction (%) |
|---|---|---|---|
| 0 | 5.7 | 2.78 | 12.7 |
| 207 | 7.7 | 2.38 | 9.6 |

Generally, it was observed that the valve leaflets constructed according to the embodiments described herein exhibited no physical or mechanical degradation, such as tears, holes, permanent set and the like, after 207 million cycles. As a result, there was also no observable change or degradation in the closed and open configurations of the valve leaflets even after 207 million cycles.

Example 2

Figure 14:
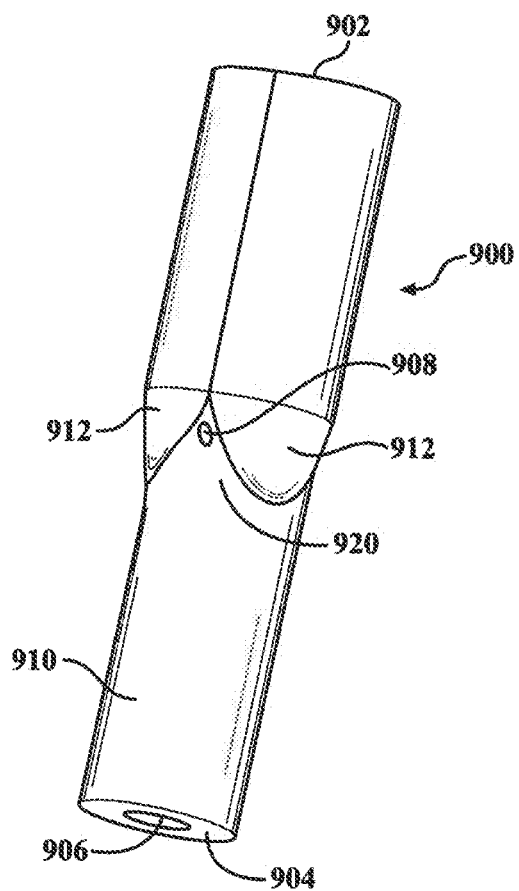
FIG. 14 is a perspective view of a mandrel for manufacturing a heart valve assembly, in accordance with an embodiment.

An embodiment of a heart valve having polymeric leaflets joined to a rigid metallic frame was constructed according to the following embodiment of a process:

A mandrel 900 was machined from PTFE having a shape shown in FIG. 14. The mandrel 900 has a first end 902 and an opposite second end 904, and extends longitudinally therebetween. The mandrel 900 has an outer surface 910 having three (two shown) generally arcuate, convex lobes 912, each generally for forming leaflets (not shown) of a finished valve assembly (not shown). The outer surface 910 also includes a frame seating area 920 for positioning a valve frame (930 in FIG. 15) relative to the convex lobes 912 prior to formation of leaflets onto the valve frame.

Figure 15:
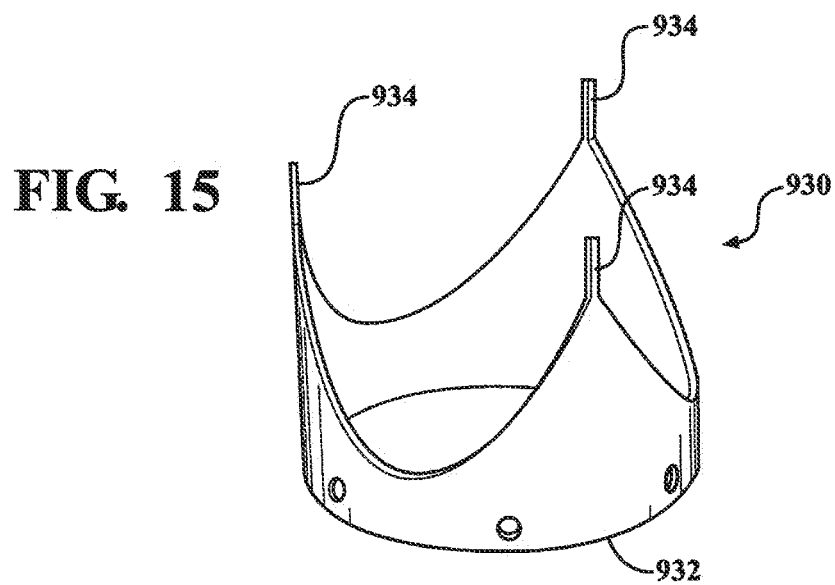
FIG. 15 is a perspective view of a valve frame for a heart valve, in accordance with an embodiment.

As shown in FIG. 15, a valve frame 930 was laser cut from a length of 316 stainless steel tube with an outside diameter of about 25.4 mm and a wall thickness of about 0.5 mm in the shape shown in FIG. 15. In the embodiment shown, the valve frame 930 extends axially between a bottom end 932 and an opposite top end defined generally by a plurality of axially extending, generally spire shaped posts 934 corresponding to the number of leaflets in the intended finished valve assembly (not shown). In the specific embodiment shown, three posts 934 are formed in the valve frame 930.

Figure 16:
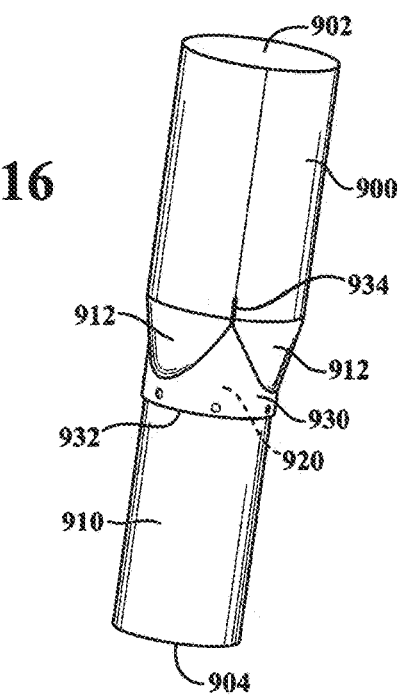
FIG. 16 is a perspective view of the valve frame of FIG. 15 nested together with the mandrel FIG. 14, in accordance with an embodiment.

Two layers of an about 4 µm thick film of FEP (not shown) was wrapped around the valve frame 930 and baked in an oven for about 30 minutes at about 270° C. and allowed to cool. The resulting covered valve frame (for clarity, shown uncovered and indicated at 930) was then slid onto the mandrel 900 so that the complementary features between the valve frame 930 and mandrel 900 are nested together, as shown in FIG. 16.

A leaflet material was then prepared having a membrane of ePTFE imbibed with a fluoroelastomer. More specifically, the membrane of ePTFE was manufactured according to the general teachings described in U.S. Pat. No. 7,306,729. The ePTFE membrane was tested in accordance with the methods described in the Appendix. The ePTFE membrane had a mass per area of about 0.57 g/m$^2$, a porosity of about 90.4%, a thickness of about 2.5 µm, a bubble point of about 458 KPa, a matrix tensile strength of about 339 MPa in the longitudinal direction and about 257 MPa in the transverse direction. This membrane was imbibed with the same fluoroelastomer as described in Example 1. The fluoroelastomer was dissolved in Novec HFE7500, 3M, St Paul, Minn., USA in an about 2.5% concentration. The solution was coated using a mayer bar onto the ePTFE membrane (while being supported by a polypropylene release film) and dried in a convection oven set to about 145° C. for about 30 seconds. After two coating steps, the resulting composite material of ePTFE/fluoroelastomer had a mass per area of about 3.6 g/m$^2$.

The composite material (not shown) was then wound around the assembled mandrel 900 and valve frame 930. In one embodiment, a total of 20 layers of the ePTFE/fluoroelastomer composite was used. Any excess composite material that extended beyond the ends of mandrel 900 were twisted and pressed lightly against the ends 902, 904 of the mandrel 900.

The composite material wrapped mandrel was then mounted in a pressure vessel so that a vent port 906 (FIG. 14) in the base or second end 904 of the mandrel 900 was plumbed to atmosphere. The vent port 906 extends from the second end 904 axially through the mandrel 900 and communicates to a generally orthogonally extending vent port 908 that extends through the outer surface 910 of the mandrel 900. The vent ports 906, 908, in addition to other vent ports which may be provided in the mandrel as needed (not shown), allow trapped air between the composite material and the mandrel to escape during the molding process.

About 690 KPa (100 psi) of nitrogen pressure was applied to the pressure vessel, forcing the ePTFE/fluoroelastomer composite against the mandrel 900 and the valve frame 930. Heat was applied to the pressure vessel until the temperature inside the vessel reached about 300° C., about 3 hours later. The heater was turned off and the pressure vessel was allowed to cool to room temperature overnight. This process thermally bonded the layers of ePTFE/fluoroelastomer composite to each other and to the FEP coating on the valve frame 930. The pressure was released and the mandrel was removed from the pressure vessel.

Figure 17:
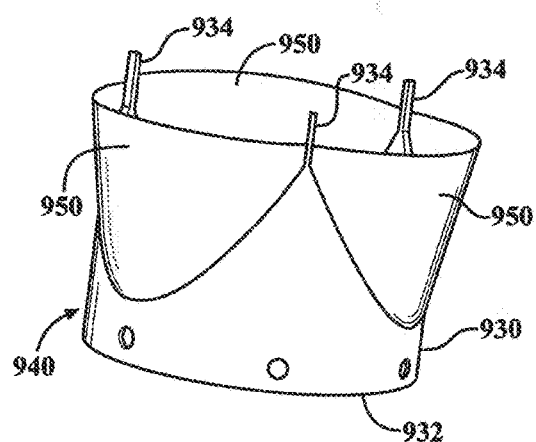
FIG. 17 is a perspective view of a molded valve, in accordance with an embodiment.

The ePTFE/fluoroelastomer composite was trimmed circumferentially in two places: first, at the bottom end 932 of the valve frame 930, and second, near the top end of the valve frame 930 along a circle generally intersecting near the mid-point of each post 934. The resulting valve assembly 940 consisting of the valve frame 930 and the trimmed composite material was separated from and slid off the mandrel The molded valve assembly 940, as shown in FIG. 17, includes the valve frame 930 and a plurality of leaflets 950 formed from the trimmed composite material. In one embodiment, the valve assembly 940 included three leaflets. In another embodiment, each leaflet 950 in the valve assembly 940 was approximately 40 µm thick.

Figure 18:
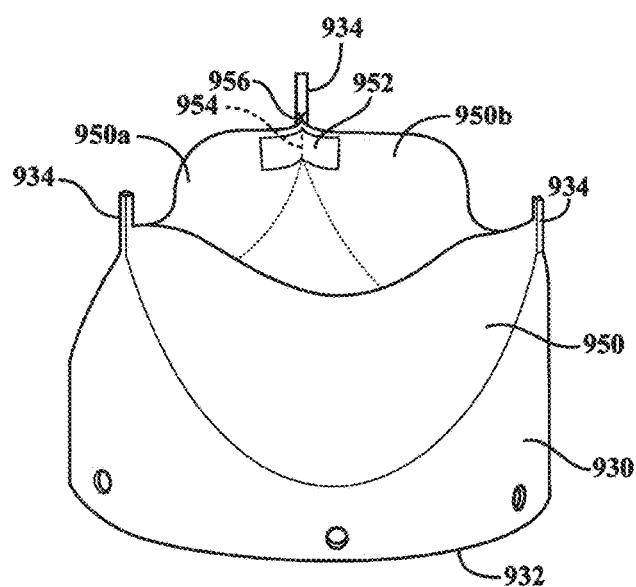
FIG. 18 is a perspective view of a molded valve, showing an attachment member for reinforcing a bond between adjacent valve leaflets and a post of a valve frame, in accordance with an embodiment.

To help control the degree of opening of the valve, adjacent leaflets about each post were bonded together. As shown in FIG. 18, the adjacent leaflets 950a, 950b were wrapped around the post 934 and bonded together to form a seam 954. The seam 954 had a depth 956 extending to at least about 2 mm from the post 934. To support the bond between the adjacent leaflets 950a, 950b, an attachment member 952 was fixedly secured to inner surfaces of the adjacent leaflets 950a, 950b thereby bridging the seam 954 between the adjacent leaflets 950a, 950b. As shown in FIG. 18, the attachment member 952 was generally rectangular. It should be appreciated, however, that other shapes for the attachment member may be utilized. The attachment member 952 was formed from the same type of composite material used to form the leaflets 950. The attachment member 952 was fixedly secured to the inner surfaces of the adjacent leaflets 950a, 950b using the fluoroelastomer solution previously described. These steps were repeated for the other pairs of adjacent leaflets of the valve assembly.

The performance and durability of the valve leaflets in this example were analyzed in the same manner as described in Example 1. The valve assembly was initially characterized on the same real-time pulse duplicator as described in Example 1 that measured typical anatomical pressures and flows across the valve, generating an initial or "zero fatigue" set of data for that particular valve assembly. The valve was then subjected to accelerated testing as in Example 1. After about 79 million cycles, the valve was removed from the high rate fatigue tester and the hydrodynamic performance again characterized as in Example 1. The valve was removed finally at about 198 million cycles. Pressure drop, EOA and regurgitant fraction measured at about 79 million cycles and about 198 cycles are summarized in Table 2 below.

Figure 13A:
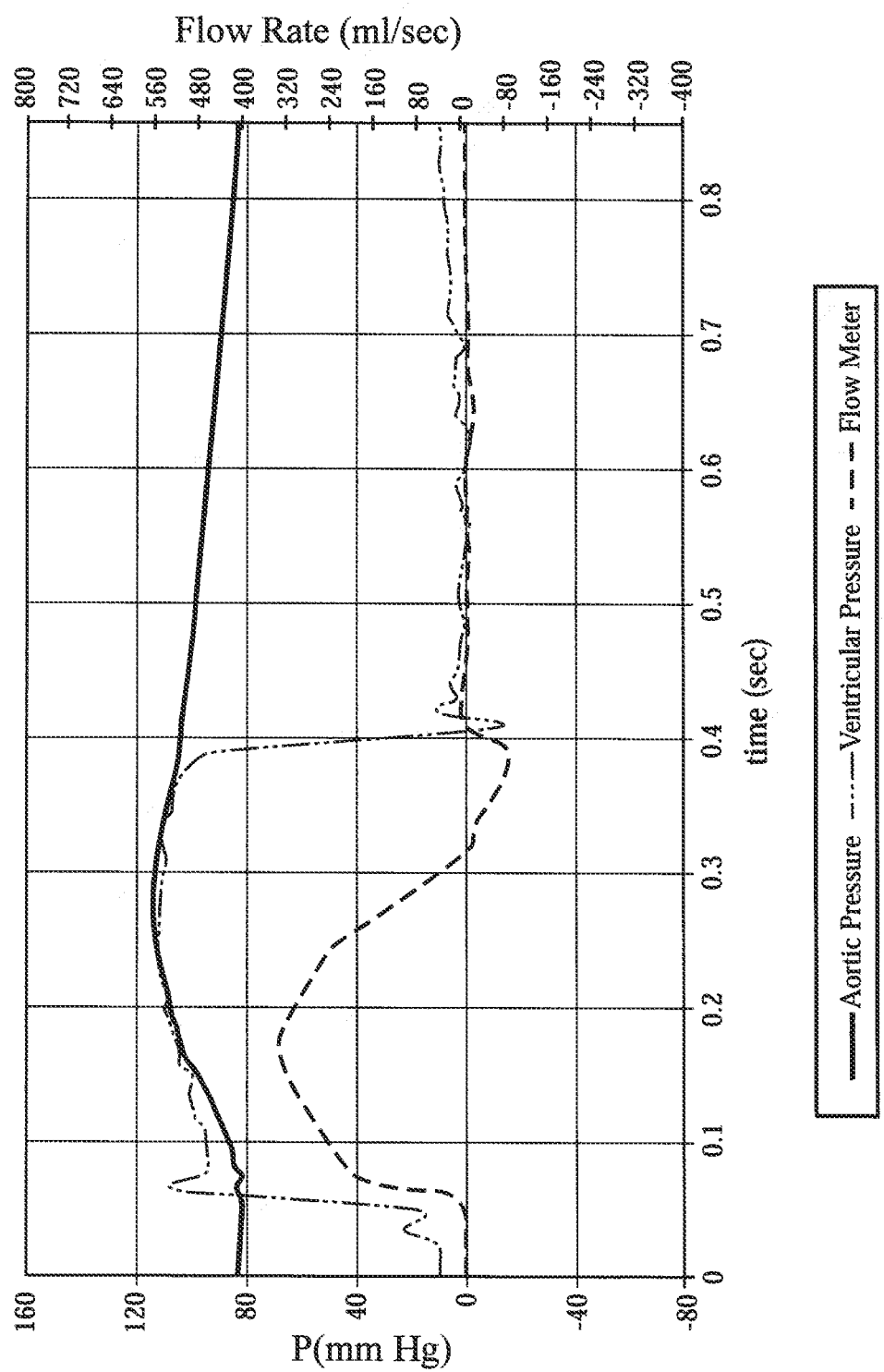
FIGS. 13A and 13B are graphs of measured outputs from the heart flow pulse duplicator system taken while testing valve assemblies made in accordance with embodiments at about 79 million cycles and after about 198 million cycles, respectively.
Figure 13B:
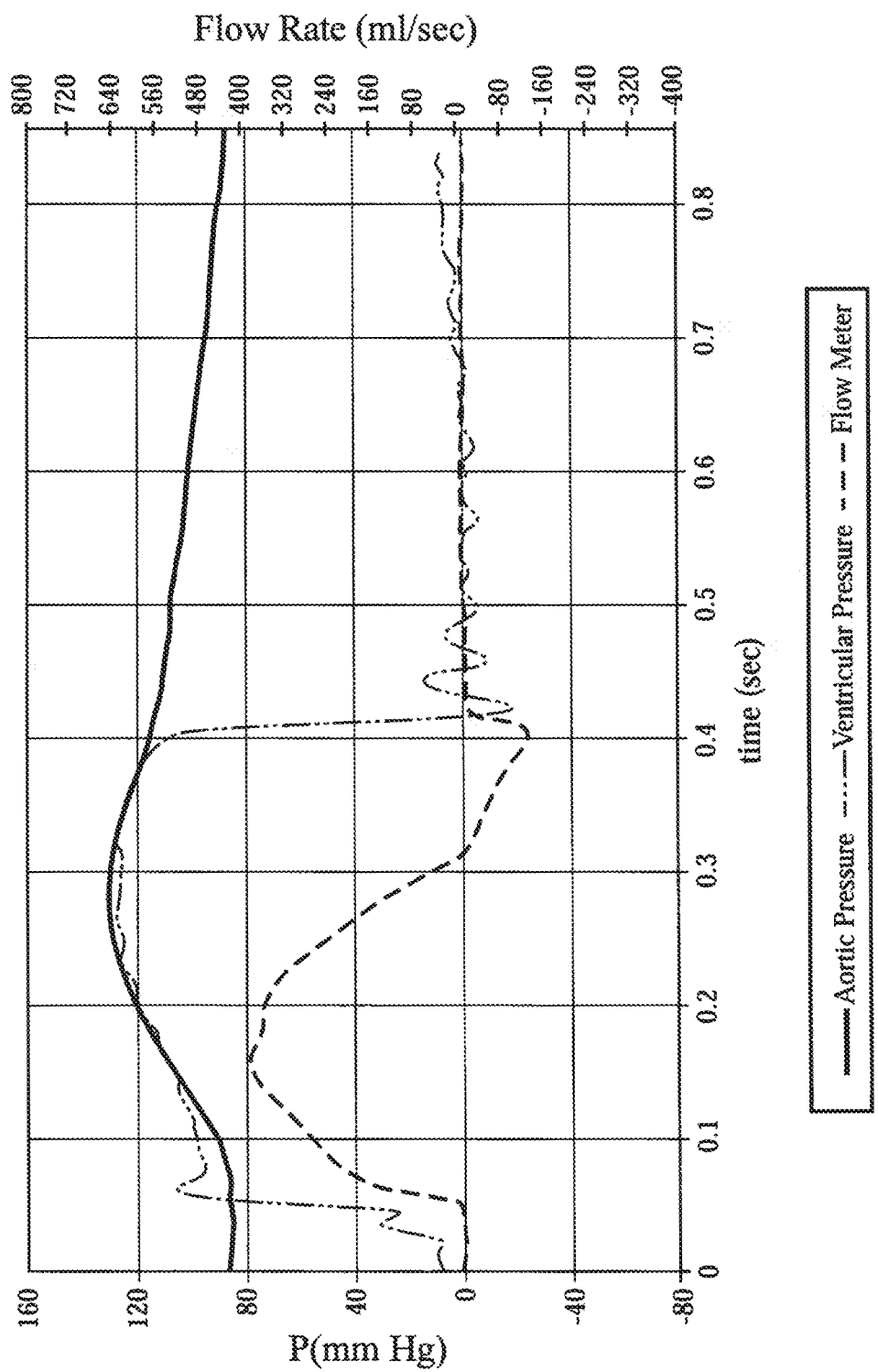

FIGS. 13A and 13B display similar results for a similar valve. FIG. 13A is a graph of measured data output from the heart flow pulse duplicator system taken after about 79 million cycles. The same measurements were taken for the similar valve after about 198 million cycles, a graph of which is shown illustratively in FIG. 13B. Both sets of measurements were taken at about 4 liters per minute flow rate and about 70 cycles per minute rate. Comparing FIGS. 13A and 13B, it should be again appreciated that the waveforms are significantly similar, indicating no substantial change in the valve leaflet performance after about 198 million cycles. Pressure drop, effective orifice area (EOA), and regurgitant fraction measured at 0, about 79, and about 198 million cycles are summarized in Table 2 below. These data indicate no substantial change in the valve leaflet performance after about 198 million cycles.

TABLE 2

| Number of Cycles (Million) | Pressure Drop (mm Hg) | EOA (cm$^2$) | Regurgitant Fraction (%) |
|---|---|---|---|
| 0 | 6.8 | 2.56 | 7.8 |
| 79 | 5.4 | 2.58 | 10.25 |
| 198 | 4.4 | 2.60 | 10.1 |

Example 3

Figure 19:
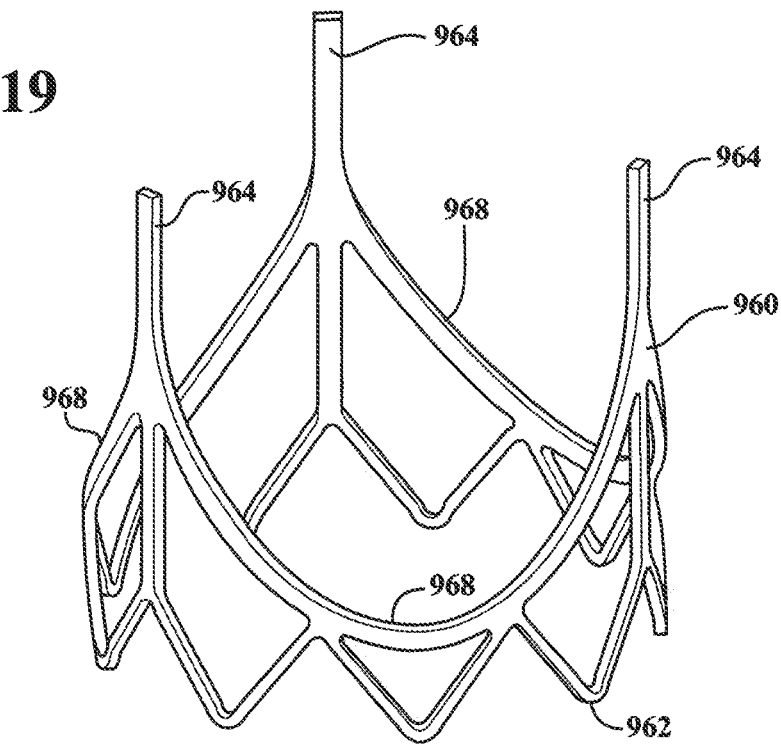
FIG. 19 is a perspective view of a valve frame, in accordance with an embodiment.

An embodiment of a heart valve having polymeric leaflets joined to a rigid metallic frame was constructed according to the following embodiment of a process:

A valve support structure or frame 960 was laser cut from a length of 316 stainless steel tube with an outside diameter of about 25.4 mm and a wall thickness of about 0.5 mm in the shape shown in FIG. 19. In the embodiment shown, the frame 960 extends axially between a bottom end 962 and an opposite top end defined generally by a plurality of axially extending, generally spire shaped posts 964 corresponding to the number of leaflets in the intended finished valve assembly (not shown). A parabolically shaped top edge 968 extends between adjacent posts 964. In the specific embodiment shown, three posts 964 and three top edges 968 form the top end of the frame 960. The corners of the frame that would be in contact with the leaflet material were rounded using a rotary sander and hand polished. The frame was rinsed with water and then plasma cleaned using a PT2000P plasma treatment system, Tri-Star Technologies, El Segundo, Calif., USA.

Figure 20:
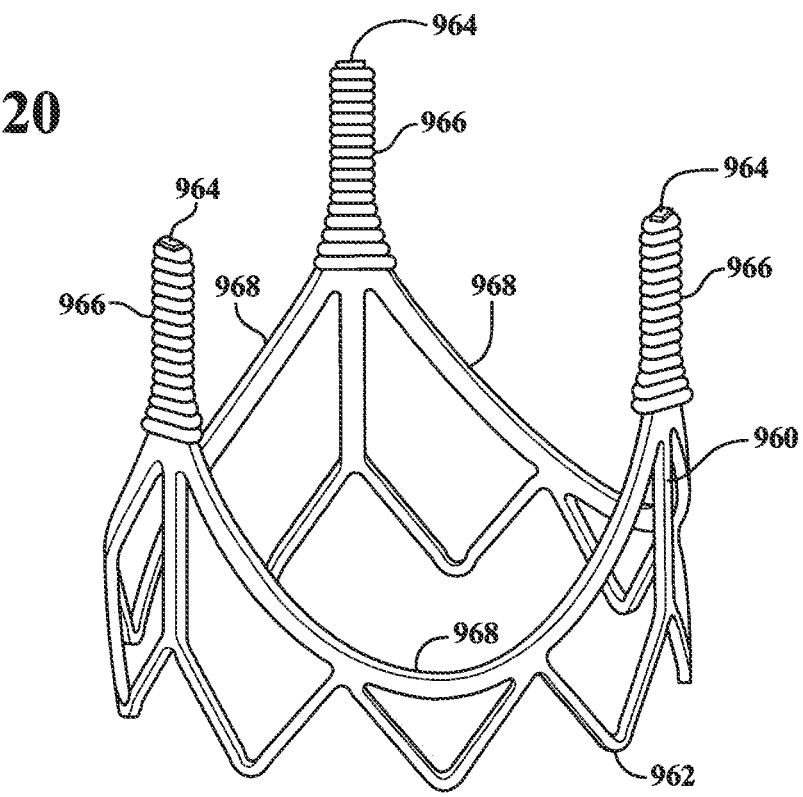
FIG. 20 is a perspective view of the valve frame of FIG. 19 with posts that are cushion-wrapped, in accordance with an embodiment.

In one embodiment, a cushion member is provided between at least a portion of the frame and at least a portion of the leaflet to minimize stress related to direct contact between the frame and the leaflet. A composite fiber of ePTFE and silicone was created by first imbibing an ePTFE membrane with silicone MED-6215 (NuSil, Carpinteria, Calif., USA), slitting it to a width of about 25 mm, and rolling into a substantially round fiber. The ePTFE used in this fiber was tested in accordance with the methods described in the Appendix. The ePTFE membrane had a bubble point of about 217 KPa, a thickness of about 10 μm, a mass per area of about 5.2 g/m$^2$, a porosity of about 78%, a matrix tensile strength in one direction of about 96 MPa, and a matrix tensile strength of about 55 MPa in an orthogonal direction. The composite fiber 966 was wrapped around each of the posts 964 of the frame 960 as shown in FIG. 20.

A mandrel 970 was formed using stereolithography in a shape shown in FIG. 21. The mandrel 970 has a first end 972 and an opposite second end 974, and extends longitudinally therebetween. The mandrel 970 has an outer surface 980 having three (two shown) generally arcuate, convex lobes 982, each generally for forming leaflets (not shown) of a finished valve assembly (not shown). The outer surface 980 also includes a frame seating area 984 for positioning the frame (960 in FIG. 19) relative to the convex lobes 982 prior to formation of the valve leaflets onto the valve frame.

The mandrel 970 was then spray coated with a PTFE mold release agent. Four layers of the ePTFE membrane previously described in this example were wrapped around the mandrel. MED-6215 was wiped onto the ePTFE and allowed to wet into and substantially fill the pores of the ePTFE. Excess MED-6215 was blotted off and the frame 960 with the composite fiber 966 wrapped posts 964 was positioned on the mandrel 970 along the frame seating area 984, as shown in FIG. 22. Silicone MED-4720, NuSil, Carpinteria, Calif., USA was placed along the top edges 968 of the frame 960 and along the posts 964 of the frame 960 to create a strain relief within the leaflet (not shown). Eight additional layers of ePTFE were wrapped around the frame 960 and mandrel 970. Additional MED-6215 was wiped onto the ePTFE and allowed to wet into and substantially fill the pores of the ePTFE. Another 8 layers of ePTFE were wrapped around the frame 960 and mandrel 970. These layers form a blotter to absorb any excess silicone during the molding process and were removed after the silicone had cured.

Silicone rubber forms (not shown) molded with one surface exactly matching the inverse shape of the mandrel surface were previously fabricated for each of the 3 leaflet-forming features. These forms were spray coated with PTFE mold release and then mated to the matching feature of the mandrel. Approximately 50 wraps of an ePTFE fiber (not shown) were wound around the silicone forms to apply generally radial pressure to the valve against the mandrel.

Figure 23:
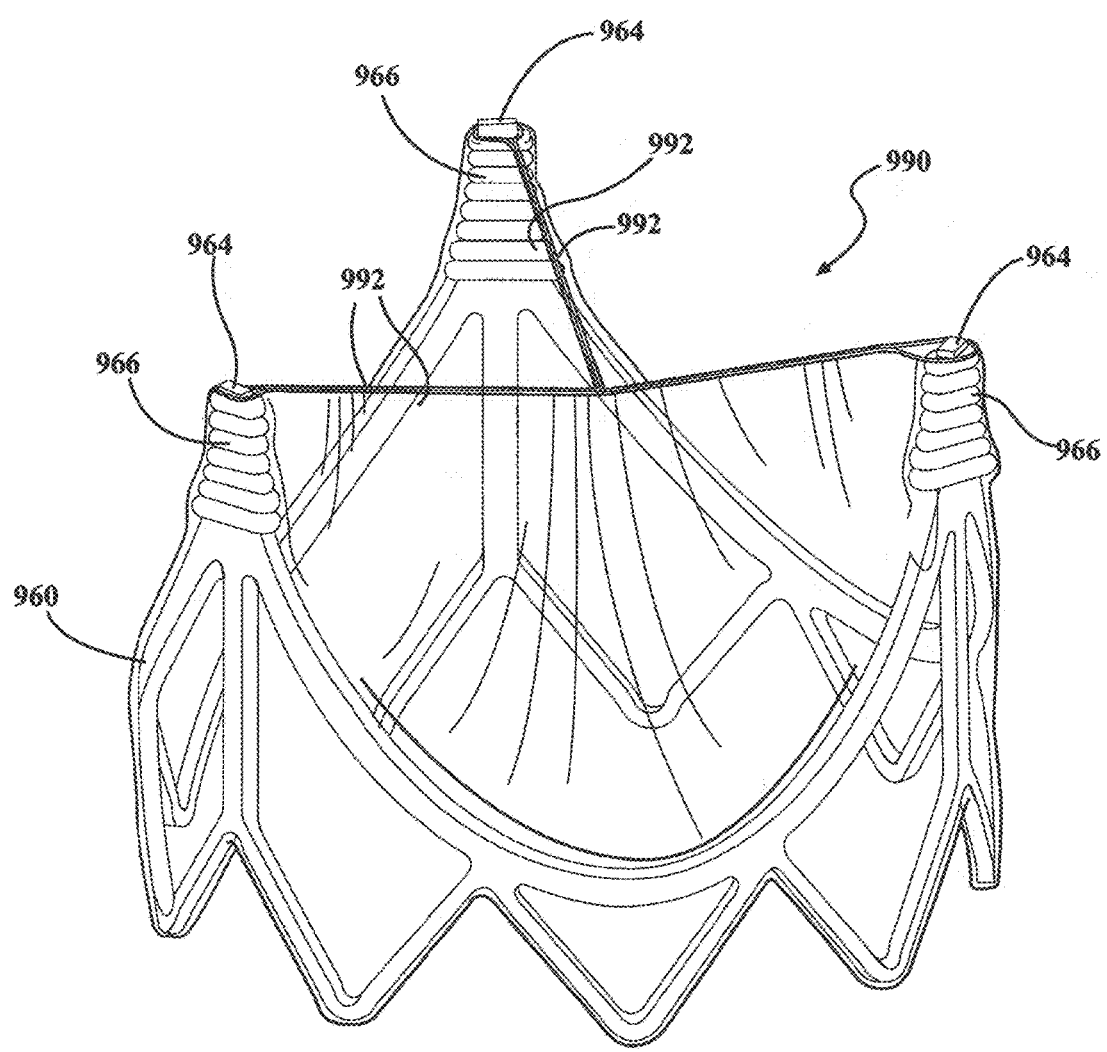
FIG. 23 is a perspective view of a valve having valve leaflets coupled to and supported on the cushion-wrapped valve frame of FIG. 20, in accordance with an embodiment.

This assembly was then placed in an oven at about 100° C. for about 1 hour to cure the silicone. After cooling, the fiber and silicone forms were removed, the 8 layers of blotter ePTFE were peeled away and discarded, and the resulting valve (not shown) was slid off of the mandrel. The posts were trimmed using wire cutters and the excess length of leaflet material and excess length of material at the base of the frame was carefully trimmed using scissors to form a completed valve assembly, which is shown and generally indicated at 990 in FIG. 23. Thus, in one embodiment, the valve assembly 990 was formed having the frame or support structure 960; a plurality of leaflets 992 supported on the support structure 960 and movable between open and closed positions to regulate blood flow through the valve assembly 990; and a composite fiber 966 wrapped post 964 located between at least a portion of the support structure 960 and at least a portion of each leaflet 992 to minimize stress in the leaflets due to the coupling and/or proximity of the leaflets to the support structure. In another embodiment, the cushion member is formed from a composite material with at least one fluoropolymer layer having a plurality of pores and an elastomer present in substantially all of the pores, as described above.

It should be appreciated that support structures other than as specifically shown in the figures may be utilized. Further, cushion members may be utilized anywhere along the support structure as necessary to minimize stress in the leaflets due to the coupling and/or proximity of the leaflets to the support structure. For example, cushion member(s) may be coupled to the support structure along the parabolically shaped top edge.

It should also be appreciated that the cushion members may be formed as sheets and wrapped around desired locations along the support structure, or be formed from fibers of various cross sectional shapes and sizes.

It should also be appreciated that the cushion members may be formed as tubes and slid over the ends of the support structure, or be slit longitudinally and positioned around the desired location along the support structure.

The leaflets of the complete valve assembly were measured and determined to have an average thickness at the center of each leaflet of about 120 μm.

The valve assembly was then characterized for flow performance and subjected to accelerated testing as in Example 1. After each block of about 50 million cycles, the valve assembly was removed from the high rate fatigue tester and the hydrodynamic performance again characterized as in Example 1. The valve assembly was removed finally at about 150 million cycles and demonstrated acceptable performance and no hole formation.

Comparative Example A

Six valves were constructed in the manner of Example 1 with the exception that the elastomer was not incorporated. The ePTFE material was the same as that described in Example 1, but it was not imbibed with the fluoroelastomer copolymer and was instead coated with a discontinuous layer of FEP copolymer that served as a thermoplastic adhesive. Valves were constructed as in Example 1 with each leaflet comprising 3 layers of membrane resulting in a final leaflet thickness averaging about 20 μm. After hydrodynamic characterization, the valves were mounted in the Dynatek accelerated tester described in Example 1. By about 40 million cycles, edge delamination and hole formation in the leaflets was observed and the test was stopped.

Comparative Example B

Two valves were constructed in the manner of Example 1 but did not incorporate the elastomer portion of the various embodiments presented herein. The material employed was thin ePTFE membrane possessing properties similar to the following: a mass per area of about 2.43 g/m$^2$, a porosity of about 88%, an IBP of about 4.8 KPa, a thickness of about 13.8 μm, a matrix tensile strength in one direction of about 662 MPa, and a matrix tensile strength of about 1.2 MPa in the orthogonal direction. The ePTFE membrane was tested in accordance with the methods described in the Appendix. Ten layers of the membrane were placed in alternating directions onto a stack and then placed on the tooling as described in Example 1. The tooling was then exposed to about 350° C. in a convection air oven for about 25 minutes, removed and quenched in a water bath. The three pieces of tooling were then inserted into the stent frame and the leaflets bonded to the valve assembly with FEP as in Example 1.

Each valve was subjected to high-rate fatigue testing using the real-time heart flow pulse duplicator system, as described above. After about 30 million cycles on one valve and about 40 million cycles on another valve, visual degradation, including stiffening and deformation, was observed and measurable decrease in performance was noted. In addition to the visual and measurable degradation in performance, Table 3 below summarizes the pressure drop, effective orifice area (EOA), and regurgitant fraction measured after about 40 million cycles.

TABLE 3

| Number of Cycles (Millions) | Pressure Drop (mm Hg) | EOA (cm$^2$) | Regurgitant Fraction (%) |
|---|---|---|---|
| 0 | 3.9 | 3.11 | 8.1 |
| 40 × 10$^6$ | 6.5 | 2.85 | 14.1 |

Example 4

Figure 24:
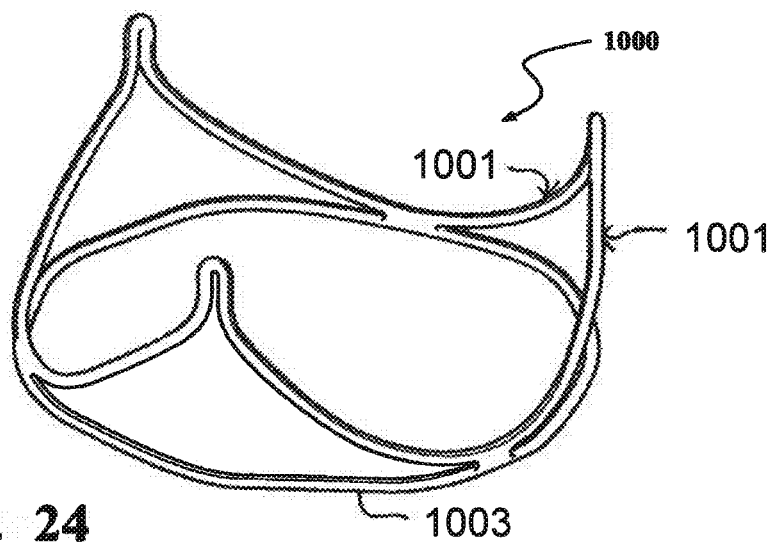
FIG. 24 is a perspective view of a valve frame, in accordance with an embodiment.

An embodiment of a heart valve having polymeric leaflets comprising a composite material including a porous polyethylene membrane and an elastomeric material as described above, joined to a metallic valve frame, was constructed according to the following embodiment of a process:

A valve frame 1000 was laser machined from a length of seamless MP35N tubing made in accordance with ASTM F.562 with a full hard temper with an outside diameter of 26 mm and a wall thickness of 0.60 mm. A pattern defining posts 1001 was cut into the tube to form the valve frame 1000, as shown in perspective view in FIG. 24.

The valve frame 1000 was lightly bead blasted to round the edges and roughen the surface. The valve frame 1000 was rinsed with water and then subjected to a plasma cleaning treatment using methods commonly known to those of ordinary skill in the art.

A composite material was then prepared having a membrane of biaxially expanded ePTFE imbibed with a silicone. More specifically, the membrane of ePTFE was manufactured according to the general teachings described in U.S. Pat. No. 3,953,566. The ePTFE membrane was tested in accordance with the methods described previously. The biaxially expanded ePTFE membrane was amorphously locked, and had the following properties: thickness=0.045 mm, density=0.499 g/cc, matrix tensile strength in the strongest direction=95.6 MPa, matrix tensile strength in the direction orthogonal to the strongest direction=31.1 MPa, elongation at maximum load in the strongest direction=37%, and elongation at maximum load in the direction orthogonal to the strongest direction=145%.

Figure 25:
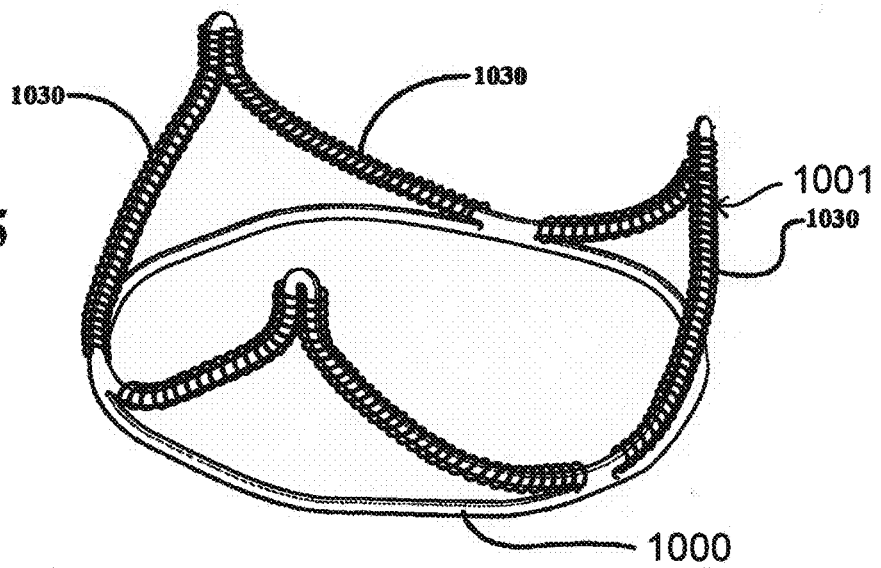
FIG. 25 is a perspective view of a valve frame with a cushion layer, in accordance with an embodiment.

This ePTFE membrane was imbibed with silicone 732 Multi-Purpose Sealant (Dow Corning, Midland, Mich.) by first coating the silicone onto a PET film using a 0.102 mm drawdown bar. The ePTFE membrane was then laid on top of the silicone coating and the silicone was allowed to wet into the membrane. A 20 mm wide strip of the composite material was removed from the PET film and rolled into a fiber and spirally wrapped around each post 1001 on the valve frame 1000 of FIG. 24, as shown in perspective view in FIG. 25. This spirally wrapped composite fiber creates a cushion member 1030 which will be located between a portion of the valve frame 1000 and the leaflet 1102 to minimize stress related to direct contact between the valve frame 1000 and the leaflet 1102, as shown in perspective view in FIG. 25.

Figure 26:
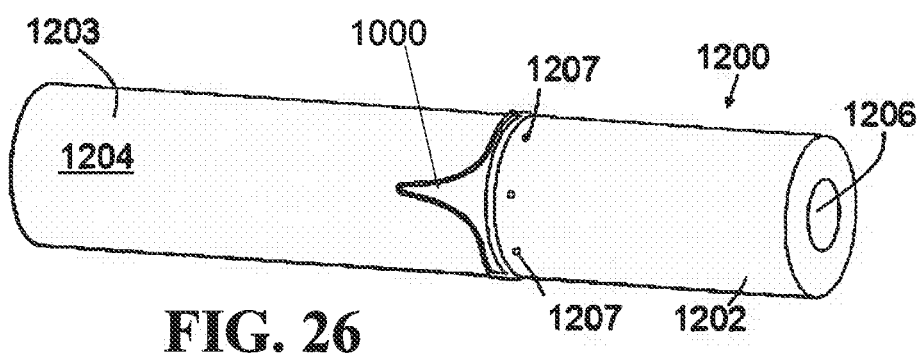
FIG. 26 is a perspective view of a mandrel, in accordance with an embodiment.

A mandrel 1200 was machined from aluminum in a generally cylindrical shape shown in perspective view in FIG. 26. The mandrel 1200 included a first end 1202 and an opposing second end 1203.

The mandrel had twelve 0.5 mm diameter holes 1207 that pass from the outer surface 1204 to a central cavity 1206 running within the center of the mandrel. Twelve holes 1207 were positioned in two rows distributed circumferentially around the mandrel, one row hidden from view by the valve frame in FIG. 26. These holes 1207, in communication with the central cavity 1206, allowed trapped air to be vented away from the valve assembly during molding.

Two layers of a sacrificial composite material comprising ePTFE and polyimide with a thickness of approximately 0.004 mm were wrapped around mandrel 1200.

A composite material was then prepared having a microporous polyethylene membrane imbibed with a silicone. The microporous polyethylene membrane was obtained from a Pall Corp. (Port Washington, N.Y.) PE Kleen 5 nm water filter cartridge ABD1UG53EJ, which contains a hydrophobic high density polyethylene (HDPE) membrane. The microporous polyethylene membrane was tested in accordance with the methods described previously and had the following properties: thickness=0.010 mm, density=0.642 g/cc, matrix tensile strength in the strongest direction=214 MPa, matrix tensile strength in the direction orthogonal to the strongest direction=174 MPa, elongation at maximum load in the strongest direction=62%, elongation at maximum load in the direction orthogonal to the strongest direction=157%, a fiber diameter of less than about 1 µm, a mean flow pore size of 0.0919 µm, and a specific surface area of 28.7 m$^2$/cc. It is anticipated that microporous polyethylene membrane may have a mean flow pore sizes of less than about 5 µm, less than about 1 µm, and less than about 0.10 µm, in accordance with embodiments.

The microporous polyethylene membrane was soaked in acetone for approximately 72 hours and allowed to air dry at room temperature. A coating of 732 Multipurpose Sealant was applied to a PET film using a 0.51 mm drawdown bar. The microporous polyethylene membrane was then laid on top of the silicone coating and the silicone was allowed to wet into the membrane. The silicone and polyethylene composite material was removed from the PET and wrapped around the mandrel 1200 and the sacrificial PTFE/Polyamide composite material, for a total of two layers.

The valve frame 1000 with posts 1001 covered by the cushion member 1030 was slid onto the mandrel 1200, on top of the two layers. Holes were poked through the previously applied layers above the vent holes and the valve frame 1000 was positioned so a base 1003 of the valve frame 1000 covered one row of the vent holes 1207 (hidden) as shown in FIG. 26.

Five more layers of the silicone/polyethylene composite material were wrapped around the valve frame 1000.

Eight layers of the ePTFE membrane previously described in this example were wrapped on top of the previous layers to create a sacrificial blotter layer to absorb any excess silicone. Two layers of a sacrificial composite material comprising ePTFE and polyimide with a thickness of approximately 0.004 mm were wrapped around the mandrel and previously applied components. Adhesive-backed polyimide tape was used to attach the ePTFE/polyimide composite to the mandrel at each end and to seal the longitudinal seam.

The mandrel 1200 with previously applied components was then mounted in a pressure vessel so that a vent port 1211 in communication with the central cavity 1206 in the first end 1202 of the mandrel 1200 was plumbed to atmosphere. The central cavity 1206 extends from the first end 1202 axially through the mandrel 1200 and in communication with the 12 previously described vent holes 1207.

Figure 27:
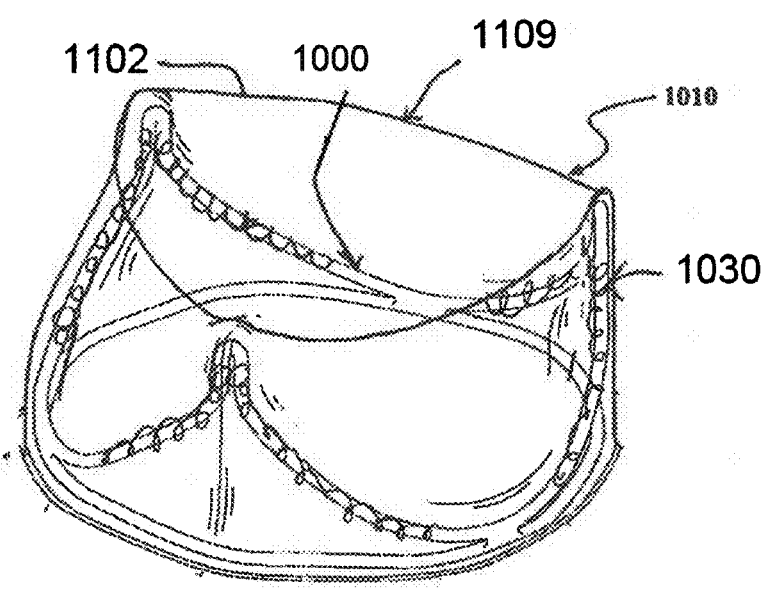
FIG. 27 is a perspective view of a valve assembly, in accordance with an embodiment.

About 414 KPa (60 psi) of helium pressure was applied to the pressure vessel, forcing the microporous polyethylene and silicone composite material against the mandrel 1200 and the valve frame 1000. Heat was applied to the pressure vessel until the temperature inside the mandrel reached about 95° C., about 28 minutes later. The heat was removed and the pressure vessel was allowed to cool to room temperature. This process bonded the layers of the silicone/polyethylene composite material to each other and to the valve frame 1000. The pressure was released and the mandrel 1200 was removed from the pressure vessel. The valve assembly 1010 was slid off of the mandrel 1200 and the outer layer of the sacrificial ePTFE/polyimide composite material was removed, as shown in perspective view in FIG. 27.

Figure 28:
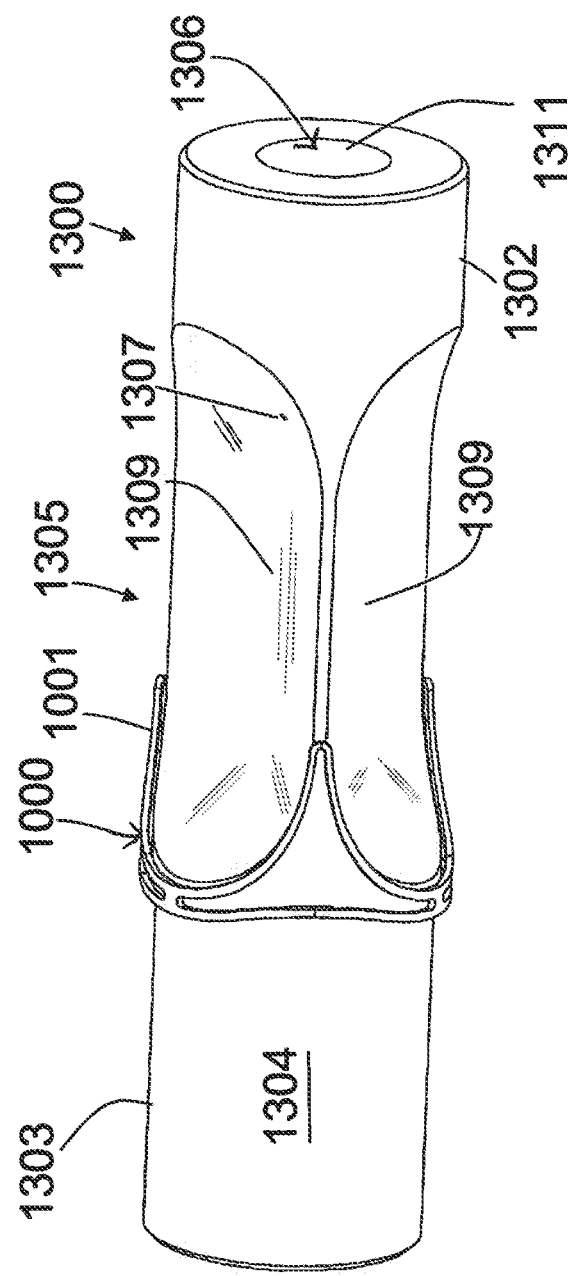
FIG. 28 is a perspective view of a mandrel, in accordance with an embodiment.

A shaped mandrel 1300 was machined from aluminum in a generally cylindrical shape shown in perspective view in FIG. 28. The mandrel 1300 includes a first end 1302, an opposing second end 1303, and a central portion 1305 therebetween defining concave features 1309.

The mandrel 1300 had three 0.5 mm diameter holes 1307 that pass from the outer surface 1304 to a central cavity 1306 running within the center of the mandrel 1300. The holes 1307 are located at the end of the concave feature closest to the shaped mandrel first end 1302, and are in communication with the central cavity 1306. These holes 1307 allowed trapped air to be vented away from the valve assembly 1010 during molding.

The valve assembly 1010 was slid onto the shaped mandrel 1300 and the valve frame 1000 was aligned with the concave features 1309 of the mandrel 1300 as shown in FIG. 28. The composite material with the sacrificial layers were pressed against the mandrel 1300 and taped to either ends of the mandrel 1300 using adhesive-backed polyimide tape. A tube of sacrificial composite material comprising ePTFE and polyimide was prepared by wrapping a sheet of the composite material around a 23.9 mm mandrel and taping the axial seam with adhesive-backed polyimide tape. This tube was slid over the valve assembly 1010 while mounted on the shaped mandrel and taped to the ends of the shaped mandrel using adhesive-backed polyimide tape.

The shaped mandrel 1300 with previously applied components was then mounted in a pressure vessel so that a vent port 1311, in communication with the central cavity 1306, in the first end 1302 of the mandrel 1300 was plumbed to atmosphere. The central cavity 1306 extends from the first end 1302 axially through the mandrel 1300 and communicates to the previously described vent holes 1307.

About 689 KPa (100 psi) of helium pressure was applied to the pressure vessel, forcing the microporous polyethylene and silicone composite material against the mandrel 1300 and the valve frame 1000. Heat was applied to the pressure vessel until the temperature inside the mandrel reached about 98° C., about 13 minutes later. The heat was removed and the pressure vessel was allowed to cool to room temperature. This process forced the layers of the silicone/polyethylene composite material to take the shape of the shaped mandrel 1300 with leaflet portions 1109 being drawn into and taking the shape of a portion of the concave features 1309. The valve assembly 1010 was slid off the mandrel 1300 and the sacrificial ePTFE/polyimide composite material and the sacrificial ePTFE blotter material was removed.

Figure 29:
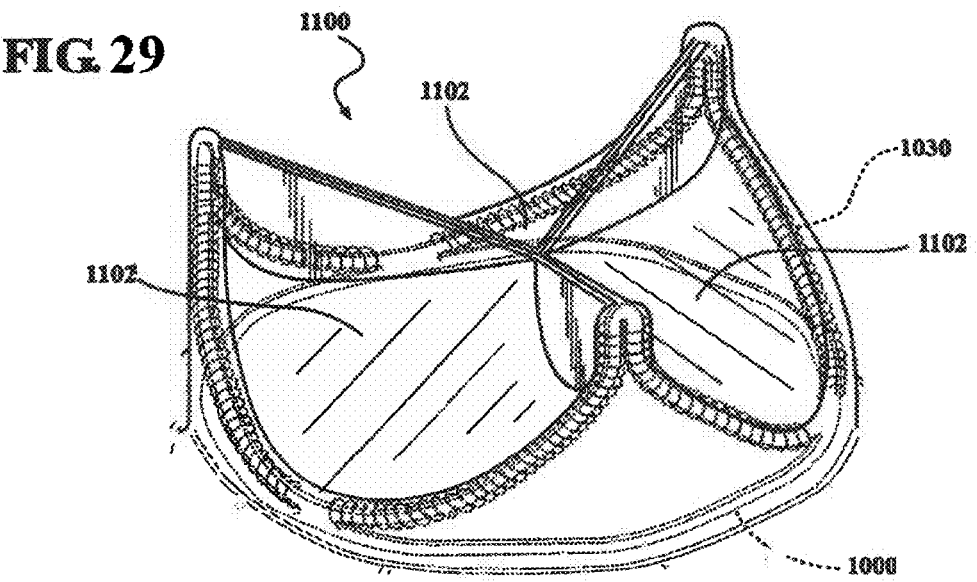
FIG. 29 is a perspective view of a valve, in accordance with an embodiment.

The microporous polyethylene and silicone composite was trimmed so that approximately 2 mm of the composite extended beyond the base of the frame and beyond the tips of the frame posts as shown in FIG. 29.

The thickness of the leaflets 1102 was approximately 139 μm and the percent weight of the silicone within the composite material was about 69%.

The performance of the valve leaflets in this valve assembly were characterized on a real-time pulse duplicator that measured typical anatomical pressures and flows across the valve, generating an initial or "zero fatigue" set of data for that particular valve assembly. The flow performance was characterized by the following process:

The valve assembly was pressed into a silicone annular ring (support structure) to allow the valve assembly to be subsequently evaluated in a real-time pulse duplicator.

The potted valve assembly was then placed into a real-time left heart flow pulse duplicator system. The flow pulse duplicator system included the following components supplied by VSI Vivitro Systems Inc., Victoria BC, Canada: a Super Pump, Servo Power Amplifier Part Number SPA 3891; a Super Pump Head, Part Number SPH 5891B, 38.320 cm$^2$ cylinder area; a valve station/fixture; a Wave Form Generator, TriPack Part Number TP 2001; a Sensor Interface, Part Number VB 2004; a Sensor Amplifier Component, Part Number AM 9991; and a Square Wave Electro Magnetic Flow Meter, Carolina Medical Electronics Inc., East Bend, N.C., USA.

In general, the flow pulse duplicator system uses a fixed displacement, piston pump to produce a desired fluid flow through the valve under test.

The heart flow pulse duplicator system was adjusted to produce the desired flow, mean pressure, and simulated pulse rate. The valve under test was then cycled for about 5 to 20 minutes.

Pressure and flow data were measured and collected during the test period, including ventricular pressures, aortic pressures, flow rates, and pump piston position.

The valve in this example had a pressure drop of 11.3 mm Hg, EOA of 2.27 cm$^2$ and regurgitant fraction of 15.4%

Example 5

Another embodiment of a heart valve having polymeric leaflets comprising a composite material including a microporous polyethylene membrane and an elastomeric material as described above, joined to a metallic valve frame, was constructed according to the following embodiment of a process:

A valve frame 1000 was prepared as in Example 4.

A composite material was prepared having a membrane of microporous polyethylene imbibed with a silicone. The microporous polyethylene membrane was obtained from a Pall Corp. (Port Washington, N.Y.) PE Kleen 5 nm water filter cartridge ABD1UG53EJ, which contains a hydrophobic high density polyethylene (HDPE) membrane. The microporous polyethylene membrane was stretched on a biaxial expansion machine. The microporous polyethylene membrane was mounted on the pins of the expansion machine with the pins positioned 70 mm apart in a first direction and 150 mm apart in the direction orthogonal to the first direction. The microporous polyethylene membrane was allowed to dwell for 60 seconds in a heated chamber within the biaxial expansion machine, reaching a web temperature of 129° C. The pins were then translated in the first direction from 70 mm to 84 mm at a rate of 0.7%/second while the pins in the direction orthogonal to the first direction were translated from 150 mm to 420 mm at a rate of 10%/second. The membrane was removed from the heated chamber while restrained by the pins and allowed to air cool to room temperature.

The stretched microporous polyethylene membrane was tested in accordance with the methods described previously and had the following properties: thickness=0.006 mm, density=0.524 g/cc, matrix tensile strength in the first direction=156 MPa, matrix tensile strength in the direction orthogonal to the first direction=474 MPa, elongation at maximum load in the first direction=167%, elongation at maximum load in the direction orthogonal to the first direction=19%, a fiber diameter of less than about 1 μm, a mean flow pore size of 0.1011 μm, and a specific surface area of 18.3 m$^2$/cc. It is anticipated that microporous polyethylene membrane may have a mean flow pore size of less than about 5 μm, less than about 1 μm, and less than about 0.10 μm, in accordance with embodiments.

The stretched microporous polyethylene membrane was imbibed with silicone 734 Flowable Sealant (Dow Corning, Midland, Mich.) by first coating the silicone onto a PET film using a 0.25 mm drawdown bar. The polyethylene membrane was then laid on top of the silicone coating and the silicone was allowed to wet into the membrane. A 20 mm wide strip of the composite material was removed from the PET film and rolled/twisted into a fiber and spirally wrapped around each post 1001 on the valve frame 1000 of FIG. 25. This spirally wrapped composite fiber creates a cushion member 1030 which will be located between a portion of the valve frame 1000 and the leaflet 1102 to minimize stress related to direct contact between the valve frame 1000 and the leaflet 1102, as shown in FIG. 29.

A mandrel 1200 as described in Example 1 and shown in FIG. 26 was obtained. Two layers of a sacrificial composite material comprising ePTFE and polyimide with a thickness of approximately 0.004 mm were wrapped around mandrel 1200.

A composite material of stretched microporous polyethylene membrane and silicone was prepared as described previously in this example.

The silicone and microporous polyethylene membrane composite material was circumferentially wrapped around the mandrel 1200 and the sacrificial PTFE/Polyamide composite material, for a total of two layers. The first direction of the stretched microporous polyethylene membrane was aligned with the long axis of the mandrel 1300 while it was wrapped.

The valve frame 1000 with fiber covered posts 1001 was slid onto the mandrel 1200, on top of the two layers. Holes were poked through the previously applied layers above the vent holes and the valve frame was positioned so a base 1003 of the valve frame 1000 covered one row of the vent holes 1207 (hidden) as shown in FIG. 26.

A small amount of silicone was applied by hand to the frame to provide additional adhesive between the frame and the circumferentially wrapped composite material.

Four more layers of the silicone and microporous polyethylene membrane composite material were wrapped around the valve frame 1000.

Eight layers of the ePTFE membrane previously described in Example 4 were wrapped on top of the previous layers to create a sacrificial blotter layer to absorb any excess silicone. Two layers of a sacrificial composite material comprising ePTFE and polyimide with a thickness of approximately 0.004 mm were wrapped around the mandrel and previously applied components. Adhesive-backed polyimide tape was used to attach the ePTFE/polyimide composite to the mandrel at each end and to seal the longitudinal seam.

The mandrel 1200 with previously applied components was then mounted in a pressure vessel so that a vent port 1211, in communication with the central cavity 1206, in the first end 1202 of the mandrel 1200 was plumbed to atmosphere. The central cavity 1206 extends from the first end 1202 axially through the mandrel 1200 and communicates to the 12 previously described vent holes 1207.

About 414 KPa (60 psi) of helium pressure was applied to the pressure vessel, forcing the microporous polyethylene membrane and silicone composite material against the mandrel 1200 and the valve frame 1000. Heat was applied to the pressure vessel until the temperature inside the mandrel reached about 66° C., about 20 minutes later. The heat was removed and the pressure vessel was allowed to cool to room temperature. This process bonded the layers of the silicone/polyethylene composite material to each other and to the valve frame 1000. The pressure was released and the mandrel 1200 was removed from the pressure vessel. The valve assembly 1010 was slid off of the mandrel 1200 and the outer layer of the sacrificial ePTFE/polyimide composite material was removed, as shown in perspective view in FIG. 26.

A shaped mandrel 1300 as described in Example 4 was obtained as shown in FIG. 28. The valve assembly 1010 was slid onto the shaped mandrel 1300 and the valve frame 1000 was aligned with the concave features 1309 of the mandrel 1300 as shown in FIG. 28. The silicone and microporous polyethylene membrane composite material with the sacrificial layers were pressed against the mandrel 1300 and taped to either ends of the mandrel 1300 using adhesive-backed polyimide tape. A tube of sacrificial composite material comprising ePTFE and polyimide was prepared by wrapping a sheet of the composite material around a 23.9 mm mandrel and taping the axial seam with adhesive-backed polyimide tape. This tube was slid over the valve assembly 1010 while mounted on the shaped mandrel and taped to the ends of the shaped mandrel using adhesive-backed polyimide tape.

The shaped mandrel 1300 with previously applied components was then mounted in a pressure vessel so that a vent port 1311 in the first end 1302 of the mandrel 1300 was plumbed to atmosphere.

About 551 KPa (80 psi) of air pressure was applied to the pressure vessel, forcing the microporous polyethylene and silicone composite material against the mandrel 1300 and the valve frame 1000. Heat was applied to the pressure vessel until the temperature inside the mandrel reached about 95° C., about 13 minutes later. The heat was removed and the pressure vessel was allowed to cool to room temperature. This process forced the layers of the silicone and microporous polyethylene membrane composite material to take the shape of the shaped mandrel 1300 with leaflet portions 1109 being drawn into and taking the shape of a portion of the concave features 1309. The valve assembly 1010 was slid off the mandrel 1300 and the sacrificial ePTFE/polyimide composite material and the sacrificial ePTFE blotter material was removed.

The polyethylene/silicone composite was trimmed so that approximately 2 mm of the composite extended beyond the base of the frame and beyond the tips of the frame posts as shown in FIG. 29.

The thickness of the leaflets 1102 was approximately 53 µm and the percent weight of the silicone within the composite material was about 65%.

The performance of the valve leaflets in this valve assembly were characterized on a real-time pulse duplicator that measured typical anatomical pressures and flows across the valve, generating an initial or "zero fatigue" set of data for that particular valve assembly. The flow performance was characterized by the process as described in Example 4.

The valve in this example had a pressure drop of 8.7 mm Hg, EOA of 2.49 $cm^2$ and regurgitant fraction of 16.7%.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

APPENDIX

As used in this disclosure, matrix tensile strength refers to the tensile strength of a porous fluoropolymer specimen under specified conditions. The porosity of the specimen is accounted for by multiplying the tensile strength by the ratio of density of the polymer to the density of the specimen.

The term membrane as used herein refers to a porous sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer may be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term imbibe used herein refers to any process used to at least partially fill pores with a secondary material.

For porous membrane having pores substantially filled with elastomer, the elastomer can be dissolved or degraded and rinsed away using an appropriate solvent in order to measure desired properties.

As the term "elastomer" is used herein it defines a polymer or a mixture of polymers that has the ability to be stretched to at least 1.3 times its original length and to retract rapidly to approximately its original length when released. The term "elastomeric" is intended to describe a property whereby a polymer displays stretch and recovery properties similar to an elastomer, although not necessarily to the same degree of stretch and/or recovery.

As the term "thermoplastic" is used herein it defines a polymer that is melt processable. In contrast to a thermoplastic polymer, a "thermoset" polymer is hereby defined as a polymer that solidifies or "sets" irreversibly when cured.

As used herein, the terms "fibril" and "fiber" are used interchangeably. As used herein, the terms "pores" and "interstices" are used interchangeably.

As used herein, the term synthetic polymer refers to polymer not derived from biological tissue.

The term leaflet as used herein in the context of prosthetic valves refers to a component of a one-way valve wherein the leaflet is operable to move between an open and closed position under the influence of a pressure differential. In an open position, the leaflet allows blood to flow through the valve. In a closed portion, the leaflet substantially blocks retrograde flow through the valve. In embodiments comprising multiple leaflets, each leaflet cooperates with at least one neighboring leaflet to block the retrograde flow of blood. Leaflets in accordance with embodiments provided herein comprise one or more layers of a composite.

Testing Methods

It should be understood that although certain methods and equipment are described below, any method or equipment determined suitable by one of ordinary skill in the art may be alternatively utilized.

Effective Orifice Area

One measure of the quality of a valve is the effective orifice area (EOA), which can be calculated as follows: EOA(cm$^2$)=$Q_{rms}$/(51.6*($\Delta P$)$^{1/2}$) where $Q_{rms}$ is the root mean square systolic/diastolic flow rate (cm$^3$/s) and $\Delta P$ is the mean systolic/diastolic pressure drop (mmHg).

Surface Area Per Unit Mass

As used in this application, the surface area per unit mass, expressed in units of m$^2$/g, was measured using the Brunauer-Emmett-Teller (BET) method on a Coulter SA3100Gas Adsorption Analyzer, Beckman Coulter Inc. Fullerton Calif., USA. To perform the measurement, a sample was cut from the center of the expanded fluoropolymer membrane and placed into a small sample tube. The mass of the sample was approximately 0.1 to 0.2 g. The tube was placed into the Coulter SA-Prep Surface Area Outgasser (Model SA-Prep, P/n 5102014) from Beckman Coulter, Fullerton Calif., USA and purged at about 110° C. for about two hours with helium. The sample tube was then removed from the SA-Prep Outgasser and weighed. The sample tube was then placed into the SA3100 Gas adsorption Analyzer and the BET surface area analysis was run in accordance with the instrument instructions using helium to calculate the free space and nitrogen as the adsorbate gas.

Bubble Point and Mean Flow Pore Size

Bubble point and mean flow pore size were measured according to the general teachings of ASTM F31 6-03 using a capillary flow Porometer, Model CFP 1500AEXL from Porous Materials, Inc., Ithaca N.Y., USA. The sample membrane was placed into the sample chamber and wet with SilWick Silicone Fluid (available from Porous Materials Inc.) having a surface tension of about 20.1 dynes/cm. The bottom clamp of the sample chamber had an about 2.54 cm diameter hole. Isopropyl alcohol was used as the test fluid. Using the Capwin software version 7.73.012 the following parameters were set as specified in the table below. As used herein, mean flow pore size and pore size are used interchangeably.

| Parameter | Set Point |
|---|---|
| Maxflow (cm$^3$/m) | 200000 |
| Bublflow (cm$^3$/m) | 100 |
| F/PT (old bubltime) | 50 |
| Minbpress (PSI) | 0 |
| Zerotime (sec) | 1 |
| V2incr (cts) | 10 |
| Preginc (cts) | 1 |
| Pulse delay (sec) | 2 |
| Maxpre (PSI) | 500 |
| Pulse width (sec) | 0.2 |
| Mineqtime (sec) | 30 |
| Presslew (cts) | 10 |
| Flowslew (cts) | 50 |
| Eqiter | 3 |
| Aveiter | 20 |
| Maxpdif (PSI) | 0.1 |
| Maxfdif (PSI) | 50 |
| Sartp (PSI) | 1 |
| Sartf (cm$^3$/m) | 500 |

Presence of Elastomer within the Pores

The presence of elastomer within the pores can be determined by several methods known to those having ordinary skill in the art, such as surface and/or cross section visual, or other analyses. These analyses can be performed prior to and after the removal of elastomer from the leaflet.

Diameter of Fibrils and Fibers

The average diameter of the fibrils and fibers was estimated by examining scanning electron micrographs that were obtained having at a magnification suitable for showing numerous fibrils or fibers, such as the scanning electron microscopy (SEM) micrographs of FIGS. 7A-C, 30 and 31. In the case of a composite material, it may be necessary to extract the elastomer or other material that may be filling the pores, by any suitable means, to expose the fibrils or fibers.

Mass, Thickness, and Density of ePTFE Membranes

Membrane thickness was measured by placing the membrane between the two plates of a Käfer FZ1000/30 thickness snap gauge Käfer Messuhrenfabrik GmbH, Villingen-Schwenningen, Germany. The average of the three measurements was reported.

Membrane samples were die cut to form rectangular sections about 2.54 cm by about 15.24 cm to measure the weight (using a Mettler-Toledo analytical balance model AG204) and thickness (using a Käfer Fz1000/30 snap gauge). Using these data, density was calculated with the following formula: $\rho$=m/(w*l*t), in which: $\rho$=density (g/cm$^3$), m=mass (g), w=width (cm), l=length (cm), and t=thickness (cm). The average of three measurements was reported.

Matrix Tensile Strength (MTS) of ePTFE Membranes

Tensile break load was measured using an INSTRON 122 tensile test machine equipped with flat-faced grips and a 0.445 kN load cell. The gauge length was about 5.08 cm and the cross-head speed was about 50.8 cm/min. The sample dimensions were about 2.54 cm by about 15.24 cm. For highest strength measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness was measured using the Käfer FZ1000/30 snap gauge; alternatively, any suitable means for measuring thickness may be used. The samples were then tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), where the bulk density of the PTFE was taken to be about 2.2 g/cm$^3$.

Mass, Thickness, and Density of Polyethylene Membranes

Membrane samples were die cut to form circular sections about 5.0 cm in diameter to measure the weight (using a Sartorius analytical balance model MC210P) and thickness (using a Starrett 3732×FL-1 micrometer). Using these data, density was calculated with the following formula: $\rho$=m/(w*l*t), in which: $\rho$=density (g/cm$^3$), m=mass (g), w=width (cm), l=length (cm), and t=thickness (cm). The average of three measurements was reported.

Matrix Tensile Strength (MTS) of Polyethylene Membranes

Tensile break load was measured using an INSTRON 5500R tensile test machine equipped with flat-faced grips and a 0.890 kN load cell. The gauge length was about 2.54 cm and the strain rate was approximately 1000%/min. The sample dimensions were about 0.47 cm by about 3.90 cm. For highest strength measurements, the longer dimension of the sample was oriented in the highest strength direction. For the orthogonal MTS measurements, the larger dimension of the sample was oriented perpendicular to the highest strength direction. The thickness of each sample was measured using a Starrett 3732×FL-1 micrometer; alternatively, any suitable means for measuring thickness may be used. The samples were then tested individually on the tensile tester. Five different sections of each sample were measured. The average of the Five maximum loads (i.e., peak force) measurements was reported. The longitudinal and transverse matrix tensile strengths (MTS) were calculated using the following equation: MTS=(maximum load/cross-section area)*(bulk density of polyethylene)/(density of the porous membrane), where the bulk density of the polyethylene was taken to be about 0.94 g/cm$^3$.

Flexural stiffness was measured by following the general procedures set forth in ASTM D790. Unless large test specimens are available, the test specimen must be scaled down. The test conditions were as follows. The leaflet specimens were measured on a three-point bending test apparatus employing sharp posts placed horizontally about 5.08 mm from one another. An about 1.34 mm diameter steel bar weighing about 80 mg was used to cause deflection in the y (downward) direction, and the specimens were not restrained in the x direction. The steel bar was slowly placed on the center point of the membrane specimen. After waiting about 5 minutes, the y deflection was measured. Deflection of elastic beams supported as above can be represented by: $d=F*L^3/48*El$, where F (in Newtons) is the load applied at the center of the beam length, L (meters), so L=½ distance between suspending posts, and El is the bending stiffness (Nm). From this relationship the value of El can be calculated. For a rectangular cross-section: $l=t^3*w/12$, where l=cross-sectional moment of inertia, t=specimen thickness (meters), w=specimen width (meters). With this relationship, the average modulus of elasticity over the measured range of bending deflection can be calculated.

Surface Area Measurements

The surface area per unit mass (specific surface area), expressed in units of m$^2$/g, of the microporous polymer membrane was measured using the Brunauer-Emmett-Teller (BET) method on a Coulter SA3100 Gas Adsorption Analyzer (Beckman Coulter Inc., Fullerton, Calif.). A sample was cut from the center of the microporous polymer membrane sheet and placed into a small sample tube. The mass of the sample was approximately 0.1 to 0.2 grams. The tube was placed into the Coulter SA-Prep Surface Area Outgasser, (Model SA-PREP, P/N 5102014) from Beckman Coulter Inc., Fullerton, Calif. and purged at 110 C for 2 hours with helium. The sample tube was then removed from the SA-Prep Outgasser and weighed. The sample tube was then placed into the SA3100 Gas Adsorption Analyzer and the BET surface area analysis was run in accordance with the instrument instructions using helium to calculate the free space and nitrogen as the adsorbate gas. A single measurement was recorded for each sample.

It is useful to convert the specific surface area as expressed in units of m$^2$/g to specific surface area expressed in units of m$^2$/cc in order to compare the specific surface areas of materials of different densities. To do so, multiply the specific surface area expressed in m$^2$/g by the density of the sample material expressed in g/cc. The density of PTFE was taken to be 2.2 g/cc and the density of polyethylene was taken to be 0.98 g/cc.

What is claimed is:

1. A valve, comprising:
   a support structure, and
   at least one leaflet being supported on the support structure and movable between open and closed positions, each leaflet including a composite material comprising at least one synthetic polymer membrane and an elastomer, the at least one synthetic polymer membrane comprising fibers that define space therebetween, wherein a diameter of a majority of the fibers is less than about 1 μm, the space between the fibers defining pores, the elastomer being disposed in substantially all of the pores, wherein the elastomer is a TFE/PMVE copolymer.

2. The valve of claim 1, wherein the composite material further includes a layer of the elastomer.

3. The valve of claim 1, wherein the at least one synthetic polymer membrane is fluoropolymer membrane.

4. The valve of claim 1, wherein the at least one synthetic polymer membrane is porous polyethylene membrane.

5. The valve of claim 4, wherein the porous polyethylene membrane has a matrix tensile strength in at least one direction greater than about 150 MPa.

6. The valve of claim 1, wherein the TFE/PMVE copolymer comprises essentially of between about 40 and 80 weight percent perfluoromethyl vinyl ether and complementally 60 and 20 weight percent tetrafluoroethylene.

7. The valve of claim 1, wherein the leaflet has a thickness of less than about 350 μm.

8. The valve of claim 1, wherein the composite material comprises at least one layer of the synthetic polymer membrane.

9. The valve of claim 1, wherein the composite material comprises more than two layers of the synthetic polymer membrane.

10. The valve of claim 9, wherein the leaflet comprises wrapped layers of the composite material, wherein a number of layers of the synthetic polymer membrane is defined by a number of times the composite material is overwrapped.

11. The valve of claim 10, wherein the leaflet has a ratio of leaflet thickness (μm) to number of layers of synthetic polymer membrane of less than about 20.

12. The valve of claim 10, wherein the leaflet has at least 10 layers and the composite material comprising less than about 50% synthetic polyethylene membrane by weight.

13. The valve of claim 10, wherein the leaflet has a ratio of leaflet thickness (μm) to number of layers of synthetic polymer membrane of less than about 20.

14. The valve of claim 1, wherein the support structure is selectively diametrically adjustable for endovascular delivery and deployment at a treatment site, wherein the valve is operable to be a prosthetic heart valve.

15. The valve of claim 1, wherein the pores have a pore size that is less than about 5 μm.

16. The valve of claim 1, wherein the pores have a pore size that is less than about 1 μm.

17. The valve of claim 1, wherein the pores have a pore size that is less than about 0.1 μm.

18. The valve of claim 1, wherein the diameter of a majority of the fibers is less than about 0.1 μm.

19. The valve of claim 1, wherein the at least one synthetic polymer membrane comprises substantially only of fibers.

20. The valve of claim 1, wherein the composite material comprises elastomer by weight in a range from about 10% to about 90%.

21. A valve, comprising:
a support structure, and
at least one leaflet being supported on the support structure and movable between open and closed positions, each leaflet including a composite material comprising at least one synthetic polymer membrane and an elastomer, the at least one synthetic polymer membrane comprising fibers that define space therebetween, wherein a diameter of a majority of the fibers is less than about 1 μm, the space between the fibers defining pores, the elastomer being disposed in substantially all of the pores,
a cushion member located between at least a portion of the support structure and at least a portion of the leaflet, wherein the cushion member comprises a second composite material with at least one synthetic polymer membrane having a plurality of pores and an elastomer present in substantially all of the pores.

22. The valve of claim 21, wherein the cushion member includes porous polyethylene membrane.

23. The valve of claim 21, wherein the cushion member at least partially covers the at least a portion of the support structure to provide a cushion between the at least a portion of the support structure and the leaflet.

24. The valve of claim 21, wherein the cushion member is wrapped about the at least a portion of the support structure to provide a cushion between the at least a portion of the support structure and the leaflet.

25. The valve of claim 21, wherein the support structure includes a first end and a second end opposite the first end, the second end comprising a plurality of posts extending longitudinally therefrom, wherein the cushion member is wrapped about each post to provide a cushion between the post and a portion of the leaflet coupled to at least a portion of the post.

26. A valve, comprising:
a support structure, and
at least one leaflet being supported on the support structure and movable between open and closed positions, each leaflet including a composite material comprising at least one synthetic polymer membrane and an elastomer, the at least one synthetic polymer membrane comprising fibers that define space therebetween, wherein a diameter of a majority of the fibers is less than about 1 μm, the space between the fibers defining pores, the elastomer being disposed in substantially all of the pores, wherein the composite material comprises at least one layer of the synthetic polymer membrane, wherein the at least one synthetic polymer membrane is expanded fluoropolymer membrane, wherein the elastomer is a TFE/PMVE copolymer, and wherein the valve is operable to be a prosthetic heart valve.

27. A valve, comprising:
a support structure, and
at least one leaflet being supported on the support structure and movable between open and closed positions, each leaflet including a composite material comprising at least one synthetic polymer membrane having a plurality of pores and an elastomer present in substantially all of the pores, the composite material comprising elastomer by weight in a range from about 10% to about 90%.

28. The valve of claim 27, wherein the composite material comprises less than about 70% synthetic polymer membrane by weight.

29. The valve of claim 27, wherein the composite material comprises less than about 60% synthetic polymer membrane by weight.

30. The valve of claim 27, wherein the composite material comprises less than about 50% synthetic polymer membrane by weight.

31. The valve of claim 27, wherein the composite material further includes a layer of an elastomer.

32. The valve of claim 27, wherein the at least one synthetic polymer membrane is fluoropolymer membrane.

33. The valve of claim 27, wherein the synthetic polymer membrane is porous polyethylene membrane.

34. The valve of claim 33, wherein the elastomer is silicone.

35. The valve of claim 33, wherein the porous polyethylene membrane has a matrix tensile strength in at least one direction greater than about 150 MPa.

36. The valve of claim 33, wherein the leaflet has at least 10 layers of porous polyethylene membrane and the composite material comprising less than about 50% synthetic polyethylene membrane by weight.

37. The valve of claim 33, wherein the pores are defined by a fibrous structure comprising fibers that have an average fiber diameter of less than about 1 μm.

38. The valve of claim 33, wherein the pores are defined by a fibrous structure comprising fibers that have an average fiber diameter of less than about 0.1 μm.

39. The valve of claim 27, wherein the elastomer is a fluoroelastomer.

40. The valve of claim 27, wherein the elastomer is a urethane.

41. The valve of claim 39, wherein the elastomer is a TFE/PMVE copolymer.

42. The valve of claim 41, wherein the TFE/PMVE copolymer consists essentially of between about 40 and 80 weight percent perfluoromethyl vinyl ether and complementally 60 and 20 weight percent tetrafluoroethylene.

43. The valve of claim 27, wherein the leaflet has a thickness of less than about 350 μm.

44. The valve of claim 27, wherein the composite material comprises at least one layer of the synthetic polymer membrane.

45. The valve of claim 44, wherein the leaflet has a ratio of leaflet thickness (μm) to number of layers of synthetic polymer membrane of less than about 20.

46. The valve of claim 27, wherein the composite material comprises more than two layers of the synthetic polymer membrane.

47. The valve of claim 46, wherein the leaflet comprises wrapped layers of the composite material, wherein a number of layers of the synthetic polymer membrane is defined by a number of times the composite material is overwrapped.

48. The valve of claim 27, wherein the pores have a pore size that is less than about 5 μm.

49. The valve of claim 27, wherein the pores have a pore size that is less than about 1 μm.

50. The valve of claim 27, wherein the pores have a pore size that is less than about 0.10 μm.

51. The valve of claim 27, further comprising:
a cushion member located between at least a portion of the support structure and at least a portion of the leaflet, wherein the cushion member comprises a second composite material with at least one synthetic polymer membrane having a plurality of pores and an elastomer present in substantially all of the pores.

52. The valve of claim 51, wherein the cushion member includes porous polyethylene membrane.

53. The valve of claim 52, wherein the cushion member is wrapped generally helically about the at least a portion of the support structure to provide a cushion between the at least a portion of the support structure and the leaflet.

54. The valve of claim 51, wherein the cushion member at least partially covers the at least a portion of the support structure to provide a cushion between the at least a portion of the support structure and the leaflet.

55. The valve of claim 51, wherein the support structure includes a first end and a second end opposite the first end, the second end comprising a plurality of posts extending longitudinally therefrom, wherein the cushion member is wrapped about each post to provide a cushion between the post and a portion of the leaflet coupled to at least a portion of the post.

56. The valve of claim 27, wherein the support structure is selectively diametrically adjustable for endovascular delivery and deployment at a treatment site.

57. The valve of claim 27, wherein the composite material comprises at least one layer of the synthetic polymer membrane, wherein the at least one synthetic polymer membrane is expanded fluoropolymer membrane, and wherein the elastomer is a TFE/PMVE copolymer.

58. The valve of claim 27, wherein the composite material comprises at least one layer of the synthetic polymer membrane, wherein the at least one synthetic polymer membrane is porous polyethylene membrane, and wherein the elastomer is a silicone.

59. A valve, comprising:
a support structure, and
at least one leaflet being supported on the support structure and movable between open and closed positions, each leaflet including a composite material comprising at least one synthetic polymer membrane and an elastomer, the at least one synthetic polymer membrane comprising fibers that define space therebetween, the space between the fibers defining pores that have a pore size that is less than about 5 μm, the elastomer being disposed in substantially all of the pores, wherein the elastomer is a TFE/PMVE copolymer.

60. The valve of claim 59, wherein the composite material further includes a layer of an elastomer.

61. The valve of claim 59, wherein the at least one synthetic polymer membrane is fluoropolymer membrane.

62. The valve of claim 59, wherein the at least one synthetic polymer membrane is porous polyethylene membrane.

63. The valve of claim 62, wherein the porous polyethylene membrane has a matrix tensile strength in at least one direction greater than about 150 MPa.

64. The valve of claim 62, wherein the leaflet has a ratio of leaflet thickness (μm) to number of layers of synthetic polymer membrane of less than about 20.

65. The valve of claim 59, wherein the TFE/PMVE copolymer comprises essentially of between about 40 and 80 weight percent perfluoromethyl vinyl ether and complementally 60 and 20 weight percent tetrafluoroethylene.

66. The valve of claim 59, wherein the leaflet has a thickness of less than about 350 μm.

67. The valve of claim 59, wherein the composite material comprises at least one layer of the synthetic polymer membrane.

68. The valve of claim 67, wherein the leaflet has a ratio of leaflet thickness (μm) to number of layers of synthetic polymer membrane of less than about 20.

69. The valve of claim 59, wherein the composite material comprises more than two layers of the synthetic polymer membrane.

70. The valve of claim 69, wherein the leaflet comprises wrapped layers of the composite material, wherein a number of layers of the synthetic polymer membrane is defined by a number of times of the composite material is overwrapped.

71. The valve of claim 59, wherein the support structure is selectively diametrically adjustable for endovascular delivery and deployment at a treatment site, wherein the valve is operable to be a prosthetic heart valve.

72. The valve of claim 59, wherein a diameter of a majority of the fibers is less than about 1 μm.

73. The valve of claim 59, wherein a diameter of a majority of the fibers is less than about 0.1 μm.

74. The valve of claim 59, wherein the pores have a pore size that is less than about 1 μm.

75. The valve of claim 59, wherein the pores have a pore size that is less than about 0.10 μm.

76. The valve of claim 59, wherein the at least one synthetic polymer membrane comprises substantially only of fibers.

77. A valve, comprising:
a support structure, and
at least one leaflet being supported on the support structure and movable between open and closed positions, each leaflet including a composite material comprising at least one synthetic polymer membrane and an elastomer, the at least one synthetic polymer membrane comprising fibers that define space therebetween, the space between the fibers defining pores that have a pore size that is less than about 5 μm, the elastomer being disposed in substantially all of the pores, wherein the composite material comprises elastomer by weight in a range from about 10% to about 90%.

78. A valve, comprising:
a support structure, and
at least one leaflet being supported on the support structure and movable between open and closed positions, each leaflet including a composite material comprising at least one synthetic polymer membrane and an elastomer, the at least one synthetic polymer membrane comprising fibers that define space therebetween, the space between the fibers defining pores that have a pore size that is less than about 5 μm, the elastomer being disposed in substantially all of the pores, wherein the composite material comprises at least one layer of the synthetic polymer membrane, wherein the leaflet has at least 10 layers of porous polyethylene membrane and the composite material comprising less than about 50% synthetic polyethylene membrane by weight.

79. A valve, comprising:
a support structure, and
at least one leaflet being supported on the support structure and movable between open and closed positions, each leaflet including a composite material comprising at least one synthetic polymer membrane and an elastomer, the at least one synthetic polymer membrane comprising fibers that define space therebetween, the space between the fibers defining pores that have a pore size that is less than about 5 μm, the elastomer being disposed in substantially all of the pores,
a cushion member located between at least a portion of the support structure and at least a portion of the leaflet, wherein the cushion member comprises a second composite material with at least one synthetic polymer membrane having a plurality of pores and an elastomer present in substantially all of the pores.

80. The valve of claim 79, wherein the cushion member includes porous polyethylene membrane.

81. The valve of claim 79, wherein the cushion member at least partially covers the at least a portion of the support structure to provide a cushion between the at least a portion of the support structure and the leaflet.

82. The valve of claim 79, wherein the cushion member is wrapped about the at least a portion of the support structure to provide a cushion between the at least a portion of the support structure and the leaflet.

83. The valve of claim 79, wherein the support structure includes a first end and a second end opposite the first end, the second end comprising a plurality of posts extending longitudinally therefrom, wherein the cushion member is wrapped about each post to provide a cushion between the post and a portion of the leaflet coupled to at least a portion of the post.

84. A valve, comprising:
a support structure, and
at least one leaflet being supported on the support structure and movable between open and closed positions, each leaflet including a composite material comprising at least one synthetic polymer membrane and an elastomer, the at least one synthetic polymer membrane comprising fibers that define space therebetween, the space between the fibers defining pores that have a pore size that is less than about 5 μm, the elastomer being disposed in substantially all of the pores, wherein the composite material comprises at least one layer of the synthetic polymer membrane, wherein the at least one synthetic polymer membrane is expanded fluoropolymer membrane, wherein the elastomer is a TFE/PMVE copolymer, and wherein the valve is operable to be a prosthetic heart valve.

85. A valve, comprising:
a support structure, and
at least one leaflet being supported on the support structure and movable between open and closed positions, each leaflet including a composite material comprising at least one synthetic polymer membrane and an elastomer, the at least one synthetic polymer membrane comprising fibers that define space therebetween, wherein a diameter of a majority of the fibers is less than about 1 μm, the space between the fibers defining pores, the elastomer being present in the pores, further comprising
a cushion member located between at least a portion of the support structure and at least a portion of the leaflet, wherein the cushion member comprises a second composite material with at least one synthetic polymer membrane having a plurality of pores and an elastomer present in the pores.

86. A valve, comprising:
a support structure, and
at least one leaflet being supported on the support structure and movable between open and closed positions, each leaflet including a composite material comprising at least one synthetic polymer membrane having a plurality of pores and an elastomer present in the pores, the composite material comprising elastomer by weight in a range from about 10% to about 90%.

87. The valve of claim 86, further comprising:
a cushion member located between at least a portion of the support structure and at least a portion of the leaflet, wherein the cushion member comprises a second composite material with at least one synthetic polymer membrane having a plurality of pores and an elastomer present in the pores.

88. A valve, comprising:
a support structure, and
at least one leaflet being supported on the support structure and movable between open and closed positions, each leaflet including a composite material comprising more than two layers of a synthetic polymer membrane and an elastomer, the synthetic polymer membrane comprising fibers that define space therebetween, wherein a diameter of a majority of the fibers is less than about 1 μm, the space between the fibers defining pores, the elastomer being disposed in substantially all of the pores, wherein the leaflet comprises overlapping wrappings of the composite material, wherein the layers of the synthetic polymer membrane are defined by a number of overlapping wrappings of the composite material, wherein the leaflet has a ratio of leaflet thickness (μm) to number of layers of synthetic polymer membrane of less than about 20.

89. A valve, comprising:
a support structure, and
at least one leaflet being supported on the support structure and movable between open and closed positions, each leaflet including a composite material comprising more than two layers of a synthetic polymer membrane and an elastomer, the at least one synthetic polymer membrane comprising fibers that define space therebetween, wherein a diameter of a majority of the fibers is less than about 1 μm, the space between the fibers defining pores, the elastomer being disposed in substantially all of the pores, wherein the leaflet comprises overlapping wrappings of the composite material, wherein the layers of the synthetic polymer membrane are defined by a number of overlapping wrappings of the composite material, wherein the leaflet has at least 10 layers and the composite material comprising less than about 50% synthetic polyethylene membrane by weight.

* * * * *